(12) United States Patent
Kouchi et al.

(10) Patent No.: US 8,073,629 B2
(45) Date of Patent: Dec. 6, 2011

(54) SIMULATION SYSTEM OF FUNCTION OF BIOLOGICAL ORGAN

(75) Inventors: Yasuhiro Kouchi, Kakogawa (JP); Takeo Saitou, Kobe (JP); Masayoshi Seike, Kobe (JP)

(73) Assignee: Sysmex Corporation, Kobe (JP)

( * ) Notice: Subject to any disclaimer, the term of this patent is extended or adjusted under 35 U.S.C. 154(b) by 1105 days.

(21) Appl. No.: 11/805,743

(22) Filed: May 24, 2007

(65) Prior Publication Data

US 2007/0288216 A1    Dec. 13, 2007

(30) Foreign Application Priority Data

May 24, 2006 (JP) ................................. 2006-144391

(51) Int. Cl.
*G06F 19/00* (2006.01)
(52) U.S. Cl. ......................................................... 702/19
(58) Field of Classification Search ........................ None
See application file for complete search history.

(56) References Cited

U.S. PATENT DOCUMENTS

| 5,971,922 | A | 10/1999 | Arita et al. |
| 2005/0234311 | A1 | 10/2005 | Kouchi et al. |
| 2005/0277015 | A1 | 12/2005 | Xu et al. |
| 2006/0025931 | A1 | 2/2006 | Rosen et al. |
| 2006/0277015 | A1 * | 12/2006 | Kouchi et al. ................. 703/11 |

FOREIGN PATENT DOCUMENTS

| CN | 1670755 A | | 9/2005 |
| JP | 2005136182 | * | 5/2005 |
| WO | WO 00/18293 | * | 4/2000 |

OTHER PUBLICATIONS

Parker et al. (AIChE Journal (2000) vol. 46, No. 12, pp. 2537-2549).*
Bergman, R. N.; Ider, Y. Z.; Bowden, C. R.; Cobelli, C. "Quantitative Estimation of Insulin Sensitivity," *American Journal of Physiology*, 1979, 236:6, E667-E677.
Bergman, R. N.; Phillips, L. S.; Cobelli, C. "Physiologic Evaluation of Factors Controlling Glucose Tolerance in Man," *Journal of Clinical Investigation*, 1981, 68:6, 1456-1467.

* cited by examiner

*Primary Examiner* — Lori A Clow
(74) *Attorney, Agent, or Firm* — Brinks Hofer Gilson & Lione

(57) ABSTRACT

A simulation system for simulating a function of a biological organ using a biological model in which the function of the biological organ are represented by a mathematical model with a computer is provided. The present system receives input of time-series actual measurement data representing the biological response of a subject, estimates the biological response of the subject at a time point at which the measurement is not performed by using the input time-series actual measurement data, and generates time-series reference data representing the biological response of the subject. The present system further generates a virtual biological organ virtually constructed in a computer system using the times-series reference data. The virtual biological organ corresponds to the function of a biological organ of the subject.

9 Claims, 29 Drawing Sheets

Template database DB

| Template | Parameter set |
|----------|---------------|
| T1 | PS#01 |
| T2 | PS#02 |
| T3 | PS#03 |
| ⋮ | ⋮ |

| Parameter | PS#01 | PS#02 | PS#03 | PS#04 |
|---|---|---|---|---|
| P01 | 77.821 | 82.033 | 94.606 | 82.379 |
| P02 | 6.5828 | 9.8641 | 9.8654 | 7.0707 |
| P03 | 55.022 | 129.14 | 92.681 | 48.874 |
| P04 | 322.68 | 158.78 | 148.37 | 283.16 |
| P05 | 0.0199 | 0.01913 | 0.019994 | 0.017849 |
| P06 | 3667 | 4402.4 | 4376.9 | 4120.8 |
| P07 | 128.84 | 96.993 | 135.67 | 79.909 |
| P08 | 0.001177 | 0.000954 | 0.000701 | 0.001951 |
| P09 | 2.1E-06 | 2.93E-06 | 5.08E-06 | 7.63E-06 |
| P10 | 3.9611 | 3.3664 | 3.9905 | 5.6773 |
| P11 | 0.19158 | 0.18024 | 0.1823 | 0.16922 |
| P12 | 0.69099 | 0.68778 | 0.68144 | 0.48112 |
| P13 | 0.024476 | 0.035714 | 0.035171 | 0.043875 |
| P14 | 0.29821 | 0.23586 | 0.30913 | 0.20052 |
| P15 | 0.049789 | 0.060879 | 0.060842 | 0.057303 |
| P16 | 0.038031 | 0.041882 | 0.068396 | 0.085411 |
| P17 | 0.034139 | 0.064749 | 0.056596 | 0.031404 |
| P18 | 0.020108 | 0.017729 | 0.017046 | 0.03625 |
| P19 | 0.000757 | 0.000657 | 0.000533 | 0.000413 | to

| | PS#97 | PS#98 | PS#99 | PS#100 |
|---|---|---|---|---|
| | 81.848 | 88.973 | 82.599 | 89.972 |
| | 8.5265 | 7.7775 | 10.056 | 9.4005 |
| | 47.889 | 107.82 | 69.734 | 127.62 |
| | 137.98 | 319.84 | 155.06 | 245.02 |
| | 0.019983 | 0.017048 | 0.018749 | 0.019162 |
| | 3444.9 | 4005.6 | 2395.5 | 4350.4 |
| | 65.597 | 56.904 | 151.51 | 61.341 |
| | 0.00205 | 0.001402 | 0.000787 | 0.001787 |
| | 2.28E-06 | 2.62E-06 | 5.4E-06 | 4.73E-06 |
| | 4.3355 | 7.0191 | 4.9057 | 7.1136 |
| | 0.15079 | 0.16955 | 0.18457 | 0.14973 |
| | 0.74786 | 0.47006 | 0.58862 | 0.59188 |
| | 0.040283 | 0.043936 | 0.024556 | 0.023531 |
| | 0.27701 | 0.18187 | 0.11489 | 0.19855 |
| | 0.047233 | 0.051684 | 0.036193 | 0.036957 |
| | 0.075596 | 0.053133 | 0.33324 | 0.03901 |
| | 0.025664 | 0.067064 | 0.04952 | 0.082559 |
| | 0.017533 | 0.042791 | 0.033157 | 0.039697 |
| | 0.000434 | 0.000769 | 0.000608 | 0.000843 |

FIG.19

| Parameter | nPS#01 | nPS#02 | nPS#03 | nPS#04 |
|---|---|---|---|---|
| P01 | 1.604557 | 1.691402 | 1.950639 | 1.698536 |
| P02 | 1.2807 | 1.919086 | 1.919339 | 1.375623 |
| P03 | 0.782674 | 1.836984 | 1.318364 | 0.69522 |
| P04 | 1.926448 | 0.94794 | 1.885791 | 1.690507 |
| P05 | 1.99 | 1.913 | 1.9994 | 1.7549 |
| P06 | 1.594348 | 1.914087 | 1.903 | 1.791652 |
| P07 | 1.6105 | 1.212413 | 1.695875 | 0.995563 |
| P08 | 1.014397 | 0.822129 | 0.604517 | 1.681552 |
| P09 | 0.50387 | 0.704591 | 1.220216 | 1.835168 |
| P10 | 1.042395 | 0.885895 | 1.050132 | 1.492974 |
| P11 | 1.987344 | 1.86971 | 1.891079 | 1.755394 |
| P12 | 1.577603 | 1.570274 | 1.555799 | 1.098447 |
| P13 | 1.112545 | 1.623364 | 1.598682 | 1.994318 |
| P14 | 1.537165 | 1.215773 | 1.593454 | 1.033608 |
| P15 | 0.743119 | 0.908642 | 0.90809 | 0.855269 |
| P16 | 0.731365 | 0.805423 | 1.315308 | 1.642519 |
| P17 | 0.812833 | 1.541643 | 1.347524 | 0.747714 |
| P18 | 0.591412 | 0.521441 | 0.501353 | 1.066176 |
| P19 | 1.610149 | 1.398128 | 1.133596 | 0.879489 | to

| nPS#97 | nPS#98 | nPS#99 | nPS#100 |
|---|---|---|---|
| 1.677278 | 1.687588 | 1.834495 | 1.703072 |
| 1.215739 | 1.658852 | 1.513132 | 1.95642 |
| 1.635562 | 0.681209 | 1.533713 | 0.991949 |
| 1.03003 | 0.823761 | 1.909493 | 0.925731 |
| 1.9285 | 1.9983 | 1.7048 | 1.8749 |
| 1.274174 | 1.497783 | 1.741565 | 1.041522 |
| 1.72575 | 0.819963 | 0.7113 | 1.893875 |
| 0.983793 | 1.767414 | 1.208621 | 0.678353 |
| 0.958678 | 0.519135 | 0.629375 | 1.29863 |
| 1.568158 | 1.140921 | 1.847132 | 1.302816 |
| 1.885166 | 1.564212 | 1.758817 | 1.914627 |
| 1.353904 | 1.707443 | 1.073196 | 1.343881 |
| 1.8015 | 1.831045 | 1.997091 | 1.116182 |
| 1.17799 | 1.427887 | 0.937474 | 0.592216 |
| 0.509776 | 0.70497 | 0.771403 | 0.540194 |
| 0.751558 | 1.453769 | 1.02788 | 0.640846 |
| 0.746095 | 0.611048 | 1.596762 | 1.179048 |
| 0.888559 | 0.515676 | 1.258559 | 0.975206 |
| 1.659191 | 0.922617 | 1.63666 | 1.293532 |

SIMULATION SYSTEM OF FUNCTION OF BIOLOGICAL ORGAN

RELATED APPLICATIONS

This application claims priority under 35 U.S.C. §119 to Japanese Patent Application No. JP2006-144391 filed May 24, 2006, the entire content of which is hereby incorporated by reference.

FIELD OF THE INVENTION

The present invention relates to a simulation system for simulating a function of a biological organ, in particular, functions of absorption, accumulation, and metabolism of glucose in biological organs, as well as functions of secretion, transport, and action of insulin using a computer.

BACKGROUND

Description using mathematical model has been attempted regarding substance concentration in biological body, in particular, blood glucose level and blood insulin concentration for medical reasons as represented by diagnosis of diabetes. The model used herein includes Bergman's minimal model (e.g., Bergman et al., American Journal of Physiology, vol. 236(6), p. E-667-77 (1979), and Bergman et al., Journal of Clinical Investigation, vol. 68(6), p. 1456-67 (1981)).

The minimal model uses blood glucose level, blood plasma insulin concentration, and insulin acting amount at the peripheral tissue insulin acting point, that is, remote insulin as variables. Assuming the blood glucose level at time t is G(t), blood plasma insulin concentration is I(t), and remote insulin is X(t), G(t), I(t), and X(t) are expressed by the following differential equations having the temporal differentiation on the left hand side.

$$dG(t)/dt = -p_1(G(t)-G_b) - X(t)G(t)$$

$$dX(t)/dt = -p_2 X(t) + p_3(I(t)-I_b)$$

$$dI(t)/dt = -n(I(t)-I_b) + \gamma(G(t)-h), \text{ (where, } G(t) > h\text{)}$$

$$= -n(I(t)-I_b) + \gamma(G(t)-h), \text{ (where } G(t) <= h\text{)}$$

Each parameter in the equation is,
$p_1$: insulin non-dependent glucose metabolic rate
$G_b$: blood glucose level base value
$p_2$: insulin intake function at insulin action point
$p_3$: insulin consumption rate with respect to insulin dependent glucose metabolism
$I_b$: insulin concentration base value
n: insulin consumption per unit time
γ: insulin secretion sensitivity with respect to glucose stimulation
h : threshold value of blood glucose level when insulin secretion starts The values differ among individuals.

Basically, four blocks of pancreas for secreting the insulin according to stimulation of blood glucose level, liver for taking up glucose from the blood or discharging glucose to blood according to the insulin concentration and the blood glucose level, circulation dynamic system for distributing insulin to peripheral tissues, and peripheral tissues for metabolizing glucose in response to the action of insulin associate with each other in the biological body to control the blood glucose level. In the minimal model, the components of the model are abstract elements that do not correspond to the four blocks of the biological body, and thus it is difficult to consider the simulation result of the change in blood glucose level and the change in insulin concentration of the biological body in association with the four blocks of the biological body.

Another blood glucose level reproducing method includes a method of predicting the blood glucose level in a diabetic patient (see e.g., U.S. Pat. No. 5,971,922). The blood glucose level may be predicted with such method, but the state of the organs related to blood glucose control is not known.

Therefore, Sysmex Corporation proposed a simulation system for obtaining the state (clinical condition) of the function of the liver such as the saccharometabolism in the liver which is effective in treating diabetes (U.S. Patent Application Publication No. 2006/0277015).

This simulation system for simulating a function of a biological organ, comprises:
a biological model in which the functions of the biological organs are expressed by mathematical models,
wherein the biological model comprises a hepatic metabolism model block having specified input and output relating to hepatic function for simulating the hepatic function, and
wherein the system further comprises arithmetic means for calculating an output value by using measurable status variables of a liver based on input value to the hepatic metabolism model block.

In such simulation system, the liver block that simulates the function of the liver outputs an output value using an actually measurable state variable, and the parameters in the mathematical model representing the function of the liver are optimized by comparing the result of simulation and the actually measured state variable. As a result, a model that represent the function of the liver more approximately is obtained, and the liver function related to liver disease is accurately simulated.

SUMMARY

The scope of the present invention is defined solely by the appended claims, and is not affected to any degree by the statements within this summary.

The first aspect of the present invention relates to a simulation system for simulating a function of a biological organ, the simulation system comprising:
input means for receiving input of time-series actual measurement data representing biological response of a subject;
reference data generating means for estimating the biological response of the subject at a time point at which the measurement is not made by using the input time-series actual measurement data, and generating time-series reference data representing the biological response of the subject; and
virtual biological organ generating means for generating a virtual biological organ virtually constructed in a computer system using the times-series reference data, the virtual biological organ corresponding to a function of a biological organ of the subject.

The second aspect of the present invention relates to a simulation system for simulating a function of a biological organ, comprising:
storing means for storing a mathematical model that comprises a plurality of parameters and represents a function of a biological organ associated with metabolism of glucose and/or insulin;
reference data generating means for estimating a biological response of a subject at a time point at which measurement of the biological response of the subject is not performed, by using actual measurement data obtained by temporally measuring biological response of the subject, and generating reference data representing the biological response of the subject; and parameter value generating means for generating a plurality of parameter values of the mathematical model by using the reference data, the mathematical model to which the parameter values are applied is capable of outputting the biological response that substantially matches the reference data generated by the reference data generating means.

The third aspect of the present invention relates to a simulation system for simulating a function of a biological organ, comprising:

storing means for storing a mathematical model that comprises a plurality of parameters and represents a function of a biological organ associated with metabolism of glucose and/or insulin;

data estimating means for estimating data of a biological response of a subject at a time point at which measurement of the biological response of the subject is not performed, by using actual measurement data obtained by temporally measuring biological response of the subject; and parameter value generating means for generating a plurality of parameter values of the mathematical model by using the actual measurement data and the estimated data, the mathematical model to which the parameter values are applied represents the function of the biological organ of the subject.

BRIEF DESCRIPTION OF THE DRAWINGS

FIG. 9 is a construction view of a template database;

FIG. 18 is a view showing 100 parameter sets that are generated;

FIG. 19 is a view showing the result of standardization process on the parameter sets of FIG. 18.

DETAILED DESCRIPTION OF THE EMBODIMENT

An embodiment of a simulation system is described hereinafter with reference to drawings.

Figure 1:
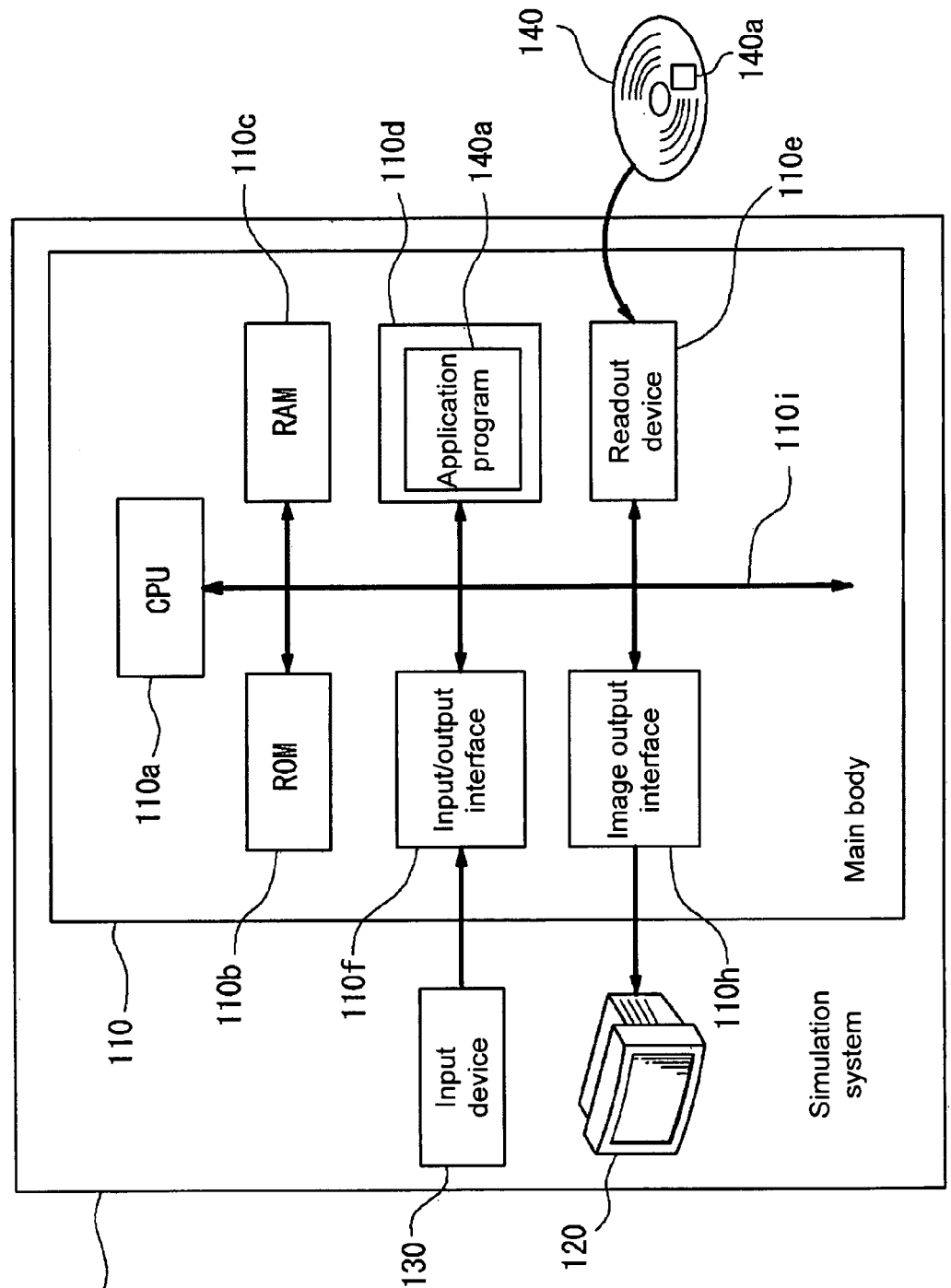
FIG. 1 is a block diagram showing hardware construction of one embodiment of a simulation system.

FIG. 1 is a block diagram showing hardware construction of the simulation system of functions of biological organs. The system 100 is composed of a computer 100a primarily comprising a main body 110, a display 120, and an input device 130. The main body 110 comprises a CPU 110a, a ROM 110b, a RAM 110c, a hard disk 110d, a readout device 110e, an input/output interface 110f, and an image output interface 110h. The CPU 110a, the ROM 110b, the RAM 110c, the hard disk 110d, the readout device 110e, the input/output interface 110f, and the image output interface 110h are data-communicably connected by a bus 110i.

The CPU 110a is capable of executing a computer program recorded in the ROM 110b and a computer program loaded in the RAM 110c. And the CPU 110a executes an application program 140a such as the above programs S2, S3 to realize each function block as described later, thereby the computer functions as the system 100.

The ROM 110b comprises mask ROM, PROM, EPROM, EEPROM, etc. and is recoded with computer programs executed by the CPU 110a and data used for the programs.

The RAM 110c comprises SRAM, DRAM, etc. The RAM 110c is used to read out computer programs recorded in the ROM 110b and the hard disk 110d. And the RAM 110c is used as a work area of the CPU 110a when these computer programs are executed.

The hard disk 110d is installed with an operating system, an application program, etc., various computer programs to be executed by the CPU 110a, and data used for executing the computer programs. The programs S2, S3 are also installed in this hard disk 110d.

The readout device 110e which comprises a flexible disk drive, a CD-ROM drive or DVD-ROM drive is capable of reading out a computer program or data recorded in a portable recording media 140. And the portable recording media 140 stores the application program 140*a* (S2, S3) to function as a system of the present invention. The computer reads out the application program 140*a* related to the present invention from the portable recording media 140 and is capable of installing the application program 140*a* in the hard disk 110*d*.

In addition to that said application program 140*a* is provided by the portable recording media 140, said application program 140*a* may be provided through an electric communication line (wired or wireless) from outside devices which are communicably connected to the computer via said electric communication line. For example, said application program 140*a* is stored in a hard disk in an application program providing server computer on the Internet to which the computer accesses and said application program 140*a* may be downloaded and installed in the hard disk 110*d*.

The hard disk 110*d* is installed with an operating system which provides a graphical user interface environment, e.g. Windows(Registered trademark) manufactured by US Microsoft Corp. In the explanation hereinafter, the application program 140*a* (S2, S3) related to this embodiment shall operate on said operating system.

The input/output interface 110*f* comprises a serial interface, e.g. USB, IEEE1394, RS-232C, etc.; a parallel interface, e.g. SCSI, IDE, IEEE1284, etc.; and an analog interface, e.g. D/A converter, A/D converter, etc. The input/output interface 110*f* is connected to the input device 130 comprising a keyboard and a mouse and users capable of inputting data into the computer using the input data device 130.

The image output interface 110*h* is connected to the display 120 comprising LCD, CRT or the like so that picture signals corresponding to image data provided from the CPU 110*a* are output to the display 120. The display 120 displays a picture (screen) based on input picture signals.

[Biological Model]

Figure 2:
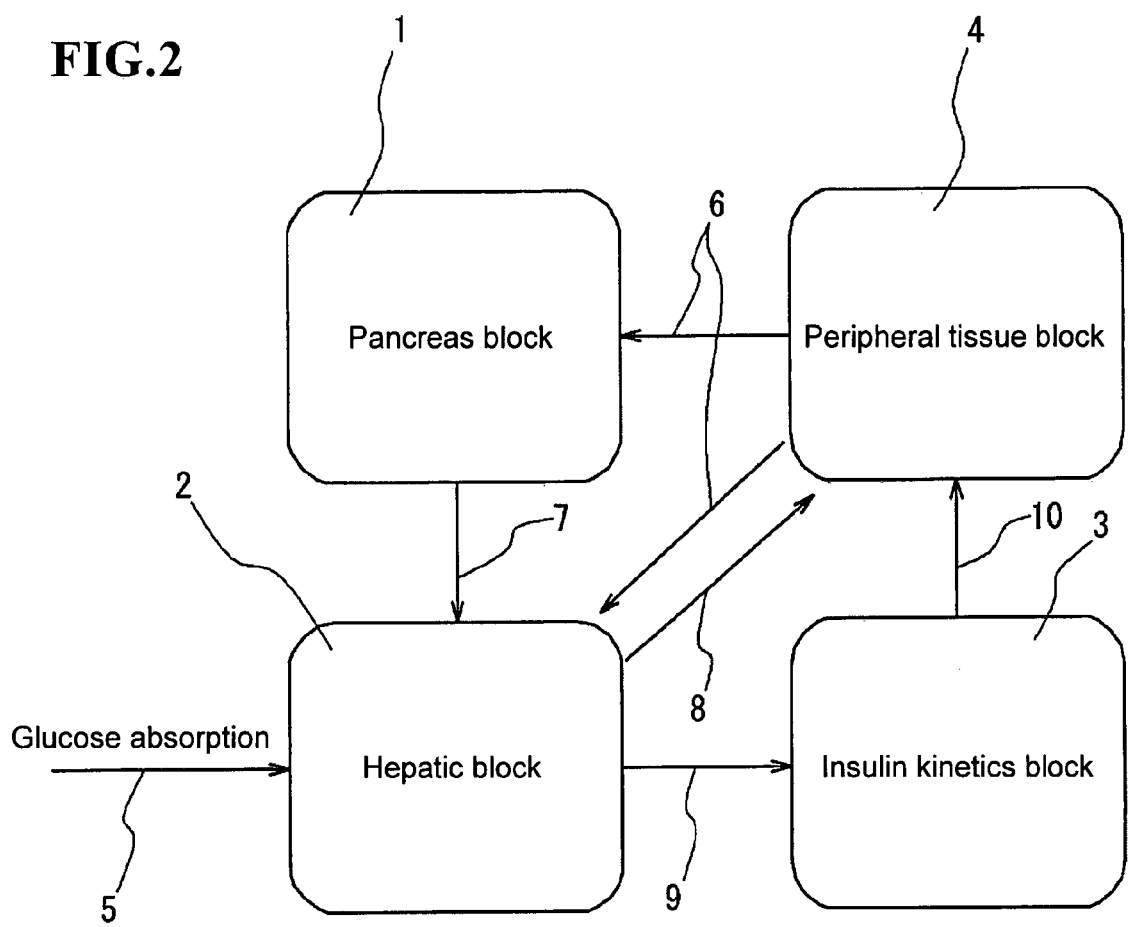
FIG. 2 is a block diagram showing overall construction of a biological model.

FIG. 2 is a block diagram showing the overall construction of one example of a biological model used in the simulation system 100 according to the present invention. The biological model, in particular, simulates biological organs associated with diabetes, and comprises a pancreas block 1, a hepatic block 2, an insulin kinetics block 3, and a peripheral tissue block 4.

Each block 1, 2, 3, 4 has input and output. As to the pancreas block 1, a blood glucose level 6 is set as input and an insulin secretion rate 7 is set as output to other blocks. As to the hepatic block 2, a glucose absorption 5 from digestive tract, a blood glucose level 6 and an insulin secretion rate 7 are set as input and net glucose release 8 and post liver insulin 9 are set as output to other blocks. As to the insulin kinetics block 3, post liver insulin 9 is set as input and peripheral tissue insulin concentration 10 is set as output to other blocks. As to the peripheral tissue block 4, a net glucose release 8, and insulin concentration 10 in the peripheral tissue are set as input and a blood glucose level 6 is set as output to other blocks.

Glucose absorption 5 is data provided from outside of the biological model. Further, the function blocks 1 to 4 are each realized by the CPU 110*a* in the simulation system 100 executing the computer program.

Next, the above-mentioned blocks each are described in detail. FGB expresses a fasting blood glucose level (FGB=BG (0)), and Ws expresses an assumed weight. DVg and DVi respectively express a distribution capacity volume against glucose and a distribution capacity volume against insulin.

[Pancreas Block of Biological Model]

Relationship between input and output of the pancreas block 1 may be expressed using the following differential equation (1). A block diagram as in FIG. 3 equivalent to the differential equation (1) may be also used.

Differential equation (1):

$$dY/dt = -\alpha\{Y(t) - \beta(BG(t) - h)\} \; (BG(t) > h)$$
$$= -\alpha Y(t) \; (BG(t) <= h)$$
$$dX/dt = -M \cdot X(t) + Y(t)$$
$$SR(t) = M \cdot X(t)$$

Variables:

BG(t): blood glucose level

X(t): total amount of insulin capable of secretion from pancreas

Y(t): supply rate of insulin newly supplied for glucose stimulation

SR(t): pancreas insulin secretion rate

Parameters:

h: threshold of glucose concentration capable of stimulating insulin supply

α: following performance to glucose stimulation

β: sensitivity to glucose stimulation

M: secretion rate per unit concentration where a blood glucose level 6 which is input to the pancreas block in FIG. 2 corresponds to BG(t). The insulin secretion rate 7 which is output of the pancreas block in FIG. 2 corresponds to SR(t).

Figure 3:
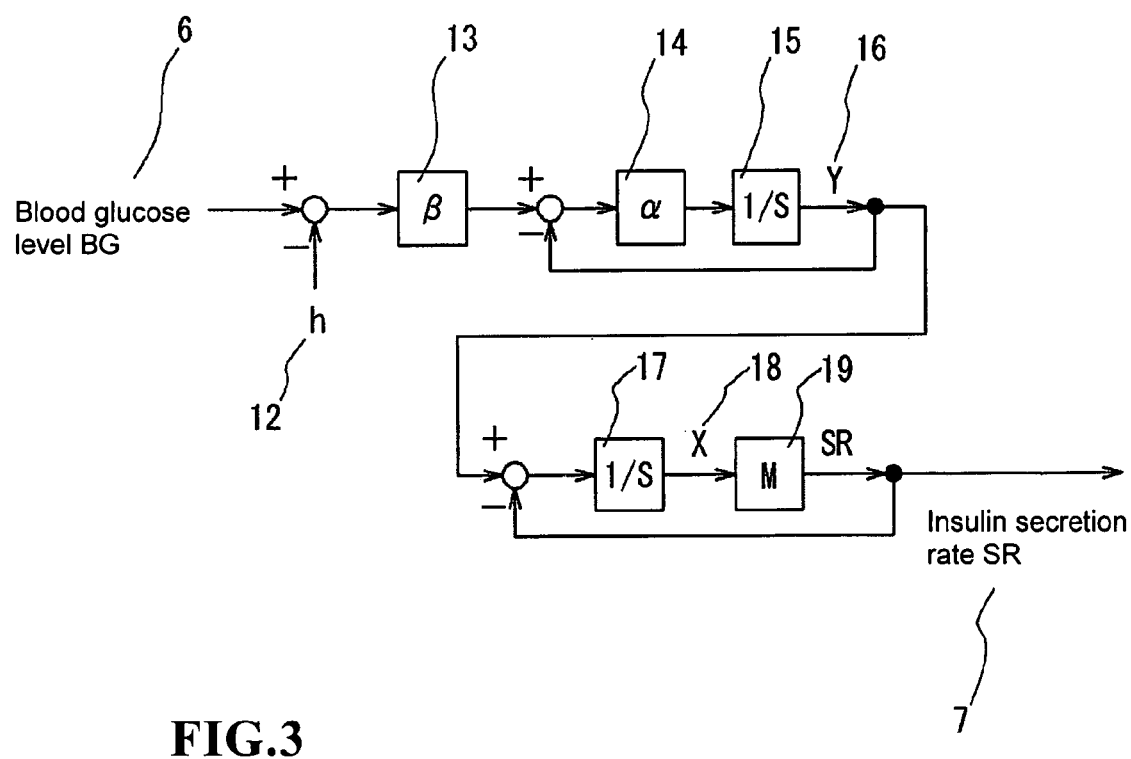
FIG. 3 is a block diagram showing a construction of pancreas model of the biological model.

In a block diagram in FIG. 3, numeral 6 indicates BG (t): blood glucose level; 7 indicates SR (t): pancreas insulin secretion rate from pancreas; 12 indicates h: glucose concentration threshold stimulating insulin supply; 13 indicates β: glucose stimulation sensitivity; 14 indicates a: glucose stimulation following capability; 15 indicates integral element; 16 indicates Y(t): supply rate of newly supplied insulin to glucose stimulation; 17 indicates integral element; 18 indicates X(t): total amount of insulin capable of secretion from pancreas; 19 indicates M: secretion rate per unit concentration.

[Hepatic Block of Biological Model]

Relationship between input and output of the hepatic block 2 may be described using the following differential equation (2). A block diagram as in FIG. 4 equivalent to the differential equation (2) may be also used.

Differential equation (2):

$$dI_4(t)/dt = \alpha 2\{-A_3 I_4(t) + (1 - A_7) \cdot SR(t)\}$$
$$Goff(FGB) = f1 \; (FGB < f3)$$
$$= f1 + f2 \cdot (FGB - f3) \; (FGB >= f3)$$
$$Func1(FGB) = f4 - f5 \cdot (FGB - f6)$$
$$Func2(FGB) = f7/FGB$$
$$b1(I_4(t)) = f8\{1 + f9 \cdot I_4(t)\}$$
$$HGU(t) = r \cdot Func1(FBG) \cdot b1(I_4(T)) \cdot RG(t) +$$
$$(1 - r) \cdot Kh \cdot BG(t) \cdot I_4(t) \; (HGU(t) >= 0)$$

-continued $$HGP(t) = I_{4off} \cdot Func2(FBG) \cdot b2 + G_{off}(FBG) -$$

$$I_4(t) \cdot Func2(FBG) \cdot b2 \; (HGP(t) >= 0)$$

$$SGO(t) = RG(t) + HGP(t) - HGU(t)$$

$$SRpost(t) = A_7 SR(t)$$

Variables:
BG(t): blood glucose level
SR(t): pancreas insulin secretion rate
SRpost(t): post hepatic insulin
RG(t): glucose absorption from digestive tract
HGP(t): hapatic glucose release
HGU (t): hepatic glucose uptake
SGO (t): net glucose from liver
I$_4$(t): hepatic insulin concentration
Parameter:
Kh: hepatic glucose uptake rate per unit insulin and unit glucose
A7: insulin uptake rate in liver
Goff: glucose release rate to basal metabolism
b2: adjustment term for hepatic glucose release suppression rate
r: insulin-dependent hepatic glucose uptake distribution rate
α2: transmission efficiency to insulin stimulation
I$_{4off}$: insulin concentration threshold of hepatic glucose release suppression
Function:
Goff (FBG): glucose release rate to basal metabolism
Func1 (FBG): hepatic glucose uptake rate to stimulation of glucose from digestive tract
Func2 (FBG): hepatic glucose release-suppression rate to insulin stimulation
f1 to f9: constants used to express the above-mentioned three elements
b1(I$_4$(t)): adjustment item for hepatic glucose incorporation rate where the glucose absorption 5 from digestive tract which is input to the hepatic block in FIG. 3 corresponds to RG(t), the blood glucose level 6 to BG(t) and the insulin secretion rate 7 to SR(t). The net glucose release 8 which is output corresponds to SGO(t) and the post liver insulin 9 to SRpost(t).

Figure 4:
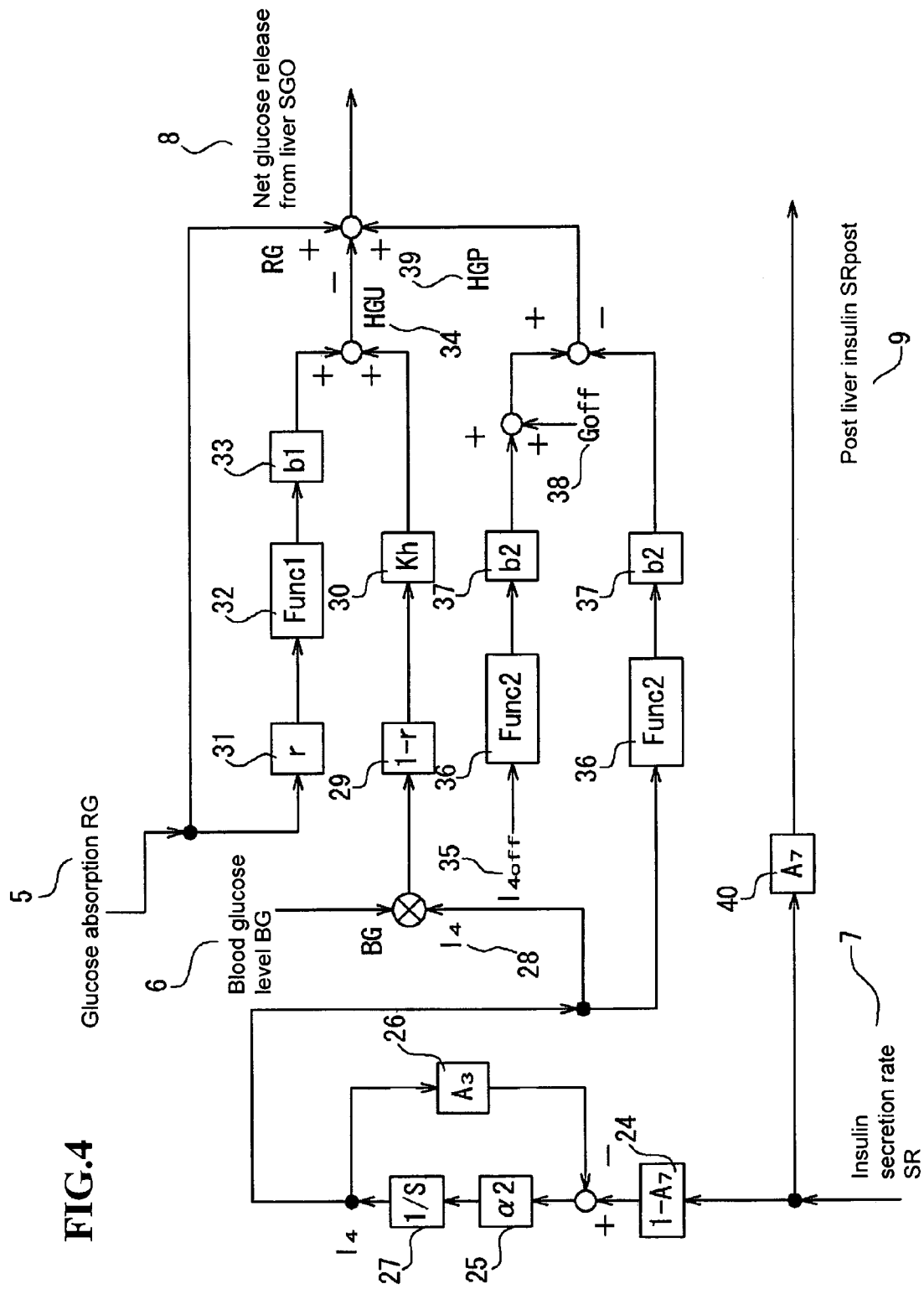
FIG. 4 is a block diagram showing a construction of a hepatic model of the biological model.

In a block diagram in FIG. 4, numeral 5 indicates RG(t): glucose absorption from digestive tract; 6 indicates BG(t): blood glucose level; 7 indicates SR(t): pancreas insulin secretion rate; 8 indicates SGO(t): net glucose from liver; 9 indicates SRpost(t): post liver insulin; 24 indicates (1-A7):liver insulin passage rate; 25 indicates α2: followability to insulin stimulation; 26 indicates A3: post liver insulin distribution rate; 27 indicates integral element; 28 indicates I4(t): hepatic insulin concentration; 9 indicates (1-r): insulin-dependant hepatic glucose incorporation distribution rate; 30 indicates Kh liver insulin-dependent glucose incorporation rate per unit insulin and unit glucose; 31 indicates r: insulin—independent hepatic glucose incorporation rate; 32 indicates Func1(FGB): hepatic glucose incorporation rate to glucose stimulation from digestive tract; 33 indicates b1 (I4(t)): adjustment item for hepatic incorporation rate; 34 indicates HGU(t): hepatic glucose incorporation; 35 indicates I4off: insulin concentration threshold of hepatic glucose release inhibition; 36 indicates Func2 (FGB): hepatic release-inhibition rate to insulin stimulation; 37 indicates b2: adjustment items hepatic glucose release-inhibition rate; 38 indicates HGP(t): glucose release rate to basal metabolism; 39 indicates A7: hepatic glucose release; 40, insulin incorporation rate in liver.

[Insulin Kinetics Block of Biological Model]

Figure 6:
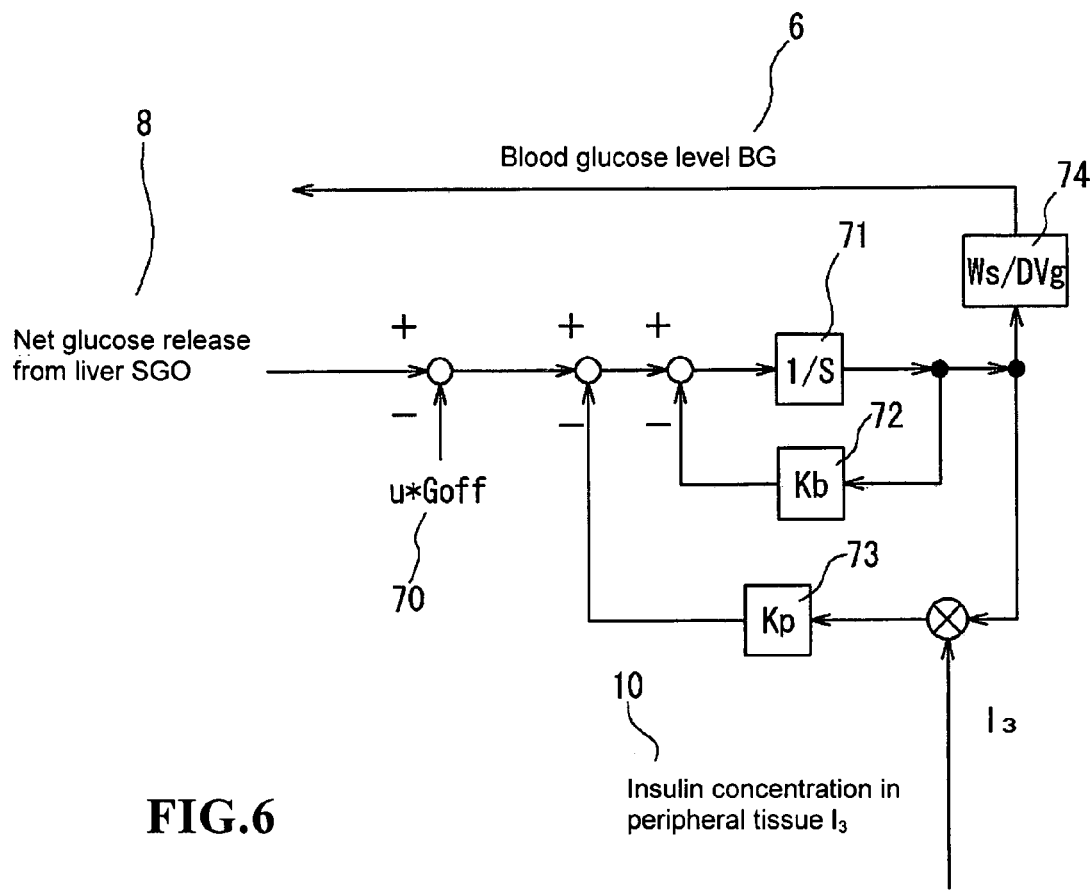
FIG. 6 is a block diagram showing a construction of a peripheral tissue model of the biological model.

Relationship between input and output of the insulin kinetics secretion may be described using the following differential equation (3). A block diagram as in FIG. 6 equivalent to the differential equation (3) may be also used.

Differential equation (3):

$$dI_1(t)/dt = -A_3 I_1(t) + A_5 I_2(t) + A_4 I_3(t) + SRpost(t)$$

$$dI_2(t)/dt = A_6 I_1(t) - A_5 I_2(t)$$

$$dI_3(t)/dt = A_2 I_1(t) - A_1 I_3(t)$$

Variables:
SRpost(t): post hepatic insulin
I$_1$(t): blood insulin concentration
I$_2$(t): insulin concentration in insulin-independent tissues
I$_3$(t): insulin concentration in peripheral tissues
Parameters:
A$_1$: insulin disappearance rate in peripheral tissues
A$_2$: insulin distribution rate to peripheral tissues
A$_3$: post hepatic insulin distribution rate
A$_4$: post peripheral tissue insulin flow out rate
A$_5$: insulin disappearance rate in insulin-independent tissues
A$_6$: insulin distribution rate to insulin-independent tissues
where the post liver insulin 9 which is input to the insulin kinetics block in FIG. 3 corresponds to SRpost(t). The peripheral tissue insulin concentration 10 which is output corresponds to I$_3$(t).

Figure 5:
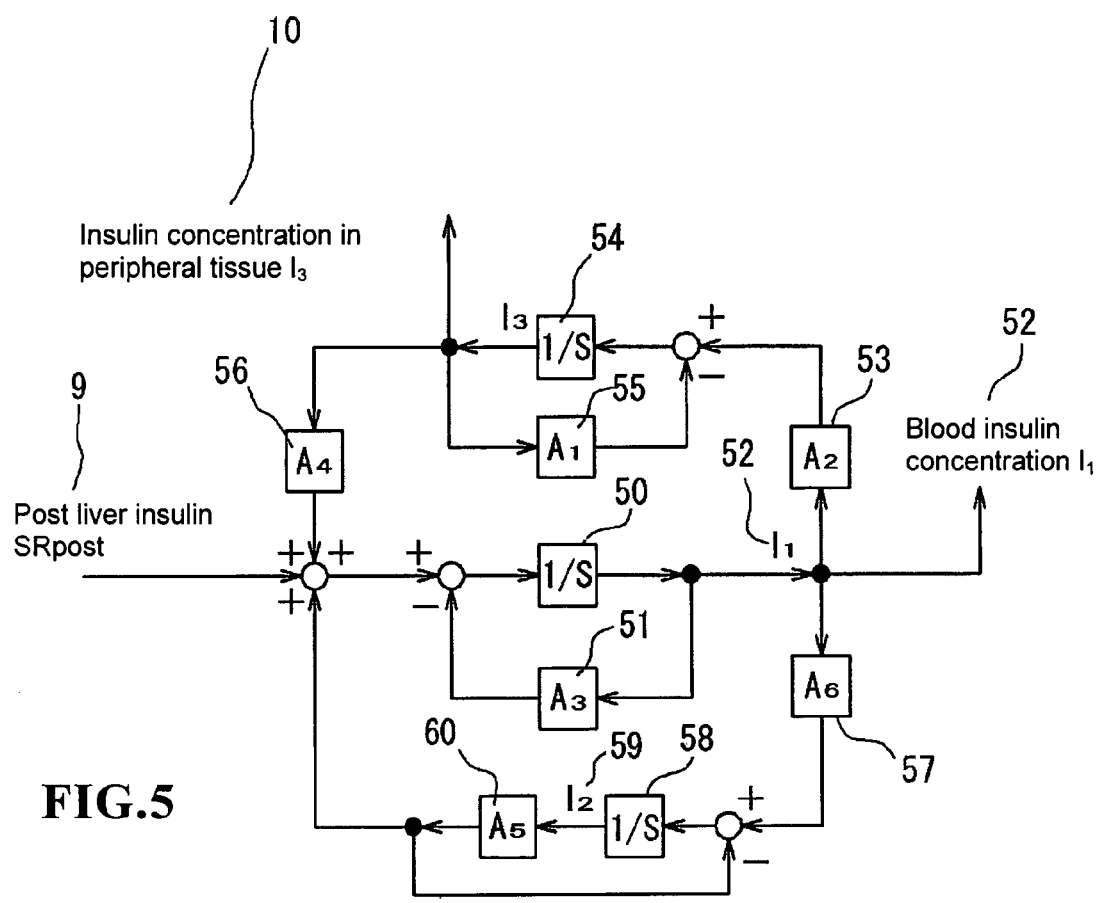
FIG. 5 is a block diagram showing a construction of insulin kinetics model of the biological model.

In a block diagram in FIG. 5, numeral 9 indicates SRpost (t): post liver insulin; 10 indicates I$_3$(t): insulin concentration in peripheral tissue; 50 indicates integral element; 51 indicates A3: post liver insulin distribution rate; 52 indicates I$_1$(t): blood insulin concentration; 53 indicates A2: insulin distribution rate to peripheral tissues; 54 indicates integral element; 55 indicates A$_1$: insulin disappearance rate in peripheral tissue; 56 indicates A$_4$: post peripheral tissue insulin discharge rate; 57 indicates A$_6$: insulin distribution rate to insulin-independent tissue; 58 indicates integral element; 59 indicates I$_2$(t): insulin concentration in insulin-independent tissue; 60 indicates A$_5$: insulin disappearance rate in insulin-independent tissue.

[Peripheral Tissue Block of Biological Model]

Relationship between input and output of the peripheral tissue block 4 may be described using the following differential equation (4). A block diagram as in FIG. 6 equivalent to the differential equation (4) may be also used.

Differential equation (4):

$$dBG'/dt = SGO(t) - u * Goff(FGB) -$$

$$Kb(BG'(t) - FBG') - Kp \cdot I3(t) \cdot BG'(t)$$

Variables:
BG'(t): blood glucose level (BG[mg/dl], BG'[mg/kg])
SGO(t): net glucose from liver
I$_3$(t): insulin concentration in peripheral tissues
FBG': fasting blood glucose (provided that FBG'=BG(0))
Parameters:
Kb: insulin-independent glucose consumption rate in peripheral tissues
Kp: insulin-dependent glucose consumption rate in peripheral tissues per unit insulin and per unit glucose u: ratio of insulin-independent glucose consumption to basal metabolism in glucose release rate to basal metabolism Functions:
Goff(FGB): glucose release rate to basal metabolism
f1 to f3: constant used to express Goff where the peripheral tissue insulin concentration 10 which is input to the peripheral tissue block in FIG. 3 corresponds to $I_3(t)$, the net glucose 8 from liver corresponds to SGO(t). The blood glucose level 6 which is output corresponds to BG(t).

Figure 7:
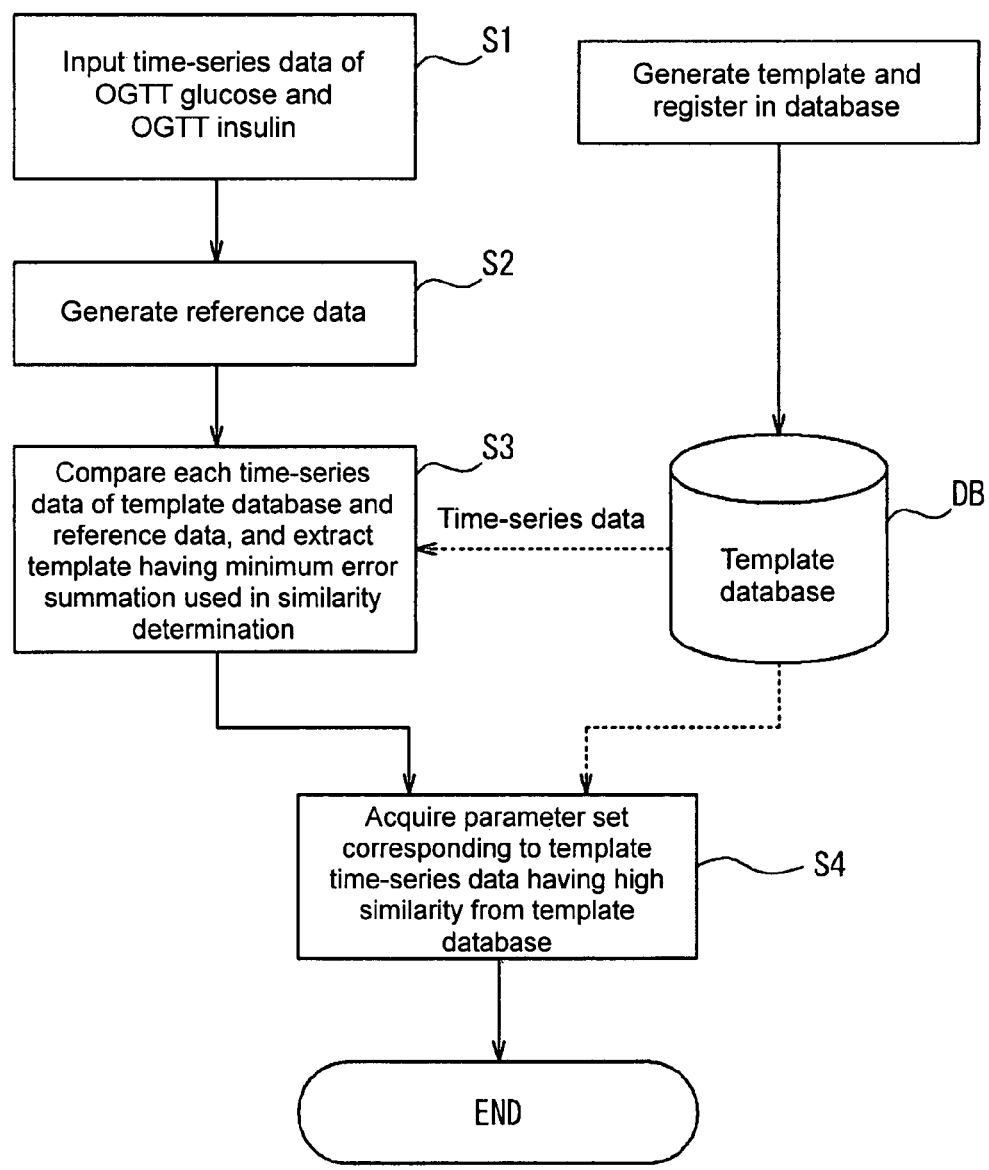
FIG. 7 is a flowchart showing procedure of a parameter set generation process.

In a block diagram in FIG. 7, numeral 6 indicates BG(t): blood glucose level; 8 indicates SGO(t): net glucose from liver; 10 indicates $I_3(t)$: insulin concentration in peripheral tissues; 70 indicates u*Goff(FGB): insulin-independent glucose consumption rate to basal metabolism; 71 indicates integral element; 72 indicates Kb: insulin-independent glucose consumption rate in peripheral tissues; 73 indicates Kp: insulin-dependent glucose consumption rate in peripheral tissues per unit insulin and per unit glucose; 74 indicates Ws/DVg: unit conversion constant.

As shown in FIG. 2, since inputs and outputs are mutually connected between the blocks constituting the present system, by giving glucose absorption 5 from digestive tract, it is possible to calculate and simulate time courses of blood glucose level and insulin concentration based on the mathematical formula.

With regard to calculation of the differential equations of the present system, e.g. E-Cell (software disclosed by Keio University) and MatLab (manufactured by The MathWorks, Inc.) may be employed. Or other calculation system may be employed.

[Generation of Biological Model]

When the result of the OGTT performed on the subject is input to the system 100, the biological model (see FIG. 2) stimulating the biological organs associated with diabetes of the subject is generated in the present system 100.

To simulate the biological organs of each subject using the above-mentioned biological models as shown in FIGS. 2 to 6, it is required to generate a biological model having characteristics suited for each subject. To be more specific, it is required to determine parameters and initial values of variables of biological model according to each subject, and apply the determined parameters and initial values to the biological model, thereby generating a biological model suited for each subject. (Unless otherwise specified, an initial value of variable is also included in parameters to be generated.)

The present system thus has a function of generating reference data or input values for the parameter set generating section to be hereinafter described using the input actual measurement data, obtaining parameter set or a set of parameters of the biological model using the reference data, and generating the biological model applied with the obtained parameter set. The parameter set generated by the parameter set generating section is applied to the biological model, and a calculating section of the system simulates the functions of the biological organs and outputs the simulated response simulating the actual biological response (test result). This function is also realized by a computer program.

[Parameter Set Generating Section]

In the following, description will be made for a parameter set generating section for forming a biological model that simulates a biological organ of a subject based on an actual OGTT (Oral Glucose Tolerance Test) result (biological response) of the subject (biological body). OGTT is a test for measuring the blood glucose level and the blood insulin concentration by orally taking glucose and taking blood a few times after a predetermined time has elapsed, and such test is actually frequently carried out since the load on the subject is small compared to glucose clamp.

[OGTT Time-Series Data Input: Step S1]

FIG. 7 is a flowchart showing procedures in which the parameter set generating section of system 100 obtains a parameter set of the biological model. In order to obtain parameters, first, an inputting step of OGTT (oral glucose tolerance test) time-series data which is an actual test result (biological response) is executed as shown in the flowchart (Step S1).

OGTT time-series data are a result of OGTT (given amount of glucose solution is orally loaded to measure the time-series of blood glucose level and blood insulin concentration) from the actual examination of the subject simulated by a biological model. Here, two data of and OGTT glucose data (blood glucose change data) and OGTT insulin (blood insulin concentration change data) are input as OGTT time-series data.

Figure 8A:
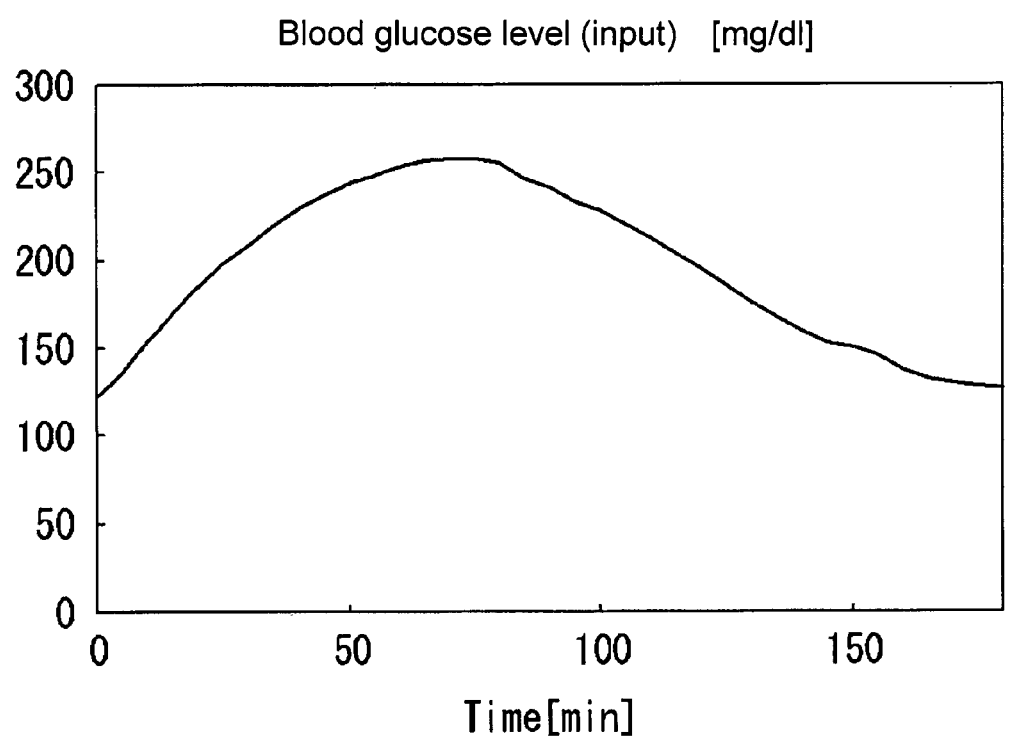
FIG. 8A is measured OGTT time-series data of blood glucose level.
Figure 8B:
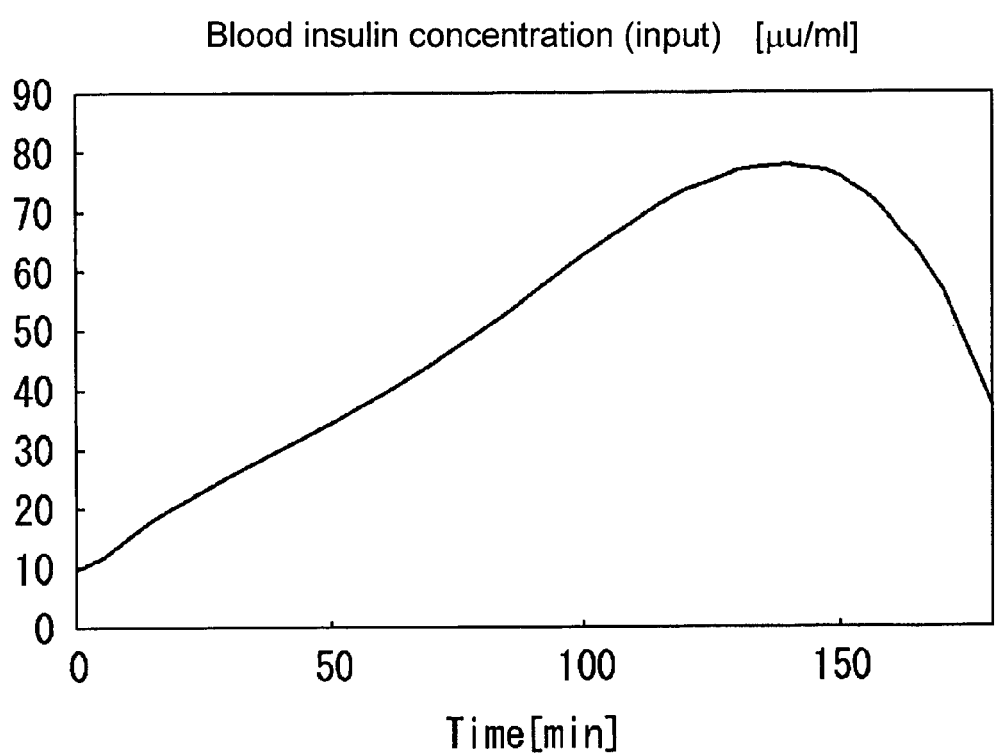
FIG. 8B is measured OGTT time-series data of blood insulin concentration.

FIG. 8A shows an example of the blood glucose level change data and FIG. 8B shows an example of the blood insulin concentration change data as OGTT time-series data to be input. In FIG. 8A, the blood glucose level change data is measured data corresponding to time course of blood glucose level BG (t), one of output items in the biological model shown in FIGS. 2 to 6. In FIG. 8B, the blood insulin concentration change data is measured data corresponding to time course of blood insulin concentration $I1(t)$, one of output items in the biological model shown in FIGS. 2 to 6.

[Generation of Reference Data: Step S2]

The reference data or the input values for the parameter set generating section is generated using the input actual measurement data (step S2). In this case, the reference data for a second time period are generated using the actual measurement data obtained during a relatively short first period. The second time period is longer than the first time period. And the reference data corresponding to the time within the range of the first time period and at which time the data is not actually measured is generated in the reference data generating section in the present system 100. Specifically, the reference data within the second time period and the reference data within the first time period are generated through interpolation based on the actual measurement data obtained within the first time period, and the estimation data at the end of the second time period equal to the actual measurement data at the start of the first time period.

In generating the biological model, a high precision biological model is obtained that may more accurately reflect the condition of the subject the greater the number of actual measurement data, in other words, the longer the time to collect the actual measurement data. However, in the case of diabetes, the OGTT data for five hours (300 min.) is barely obtained in consideration of the burden on the patient in general clinical examination scenes, and normally, the OGTT data for only two hours (120 min.) is obtained. The data is acquired only at a limited time of 0 min., 30 min., 60 min., and 120 min. within the range of two hours. However, the reference data at a greater number of times than the actual measurement data is generated through extrapolation and interpolation, which enhances the precision of simulation without placing a burden on the patient.

Figure 12A:
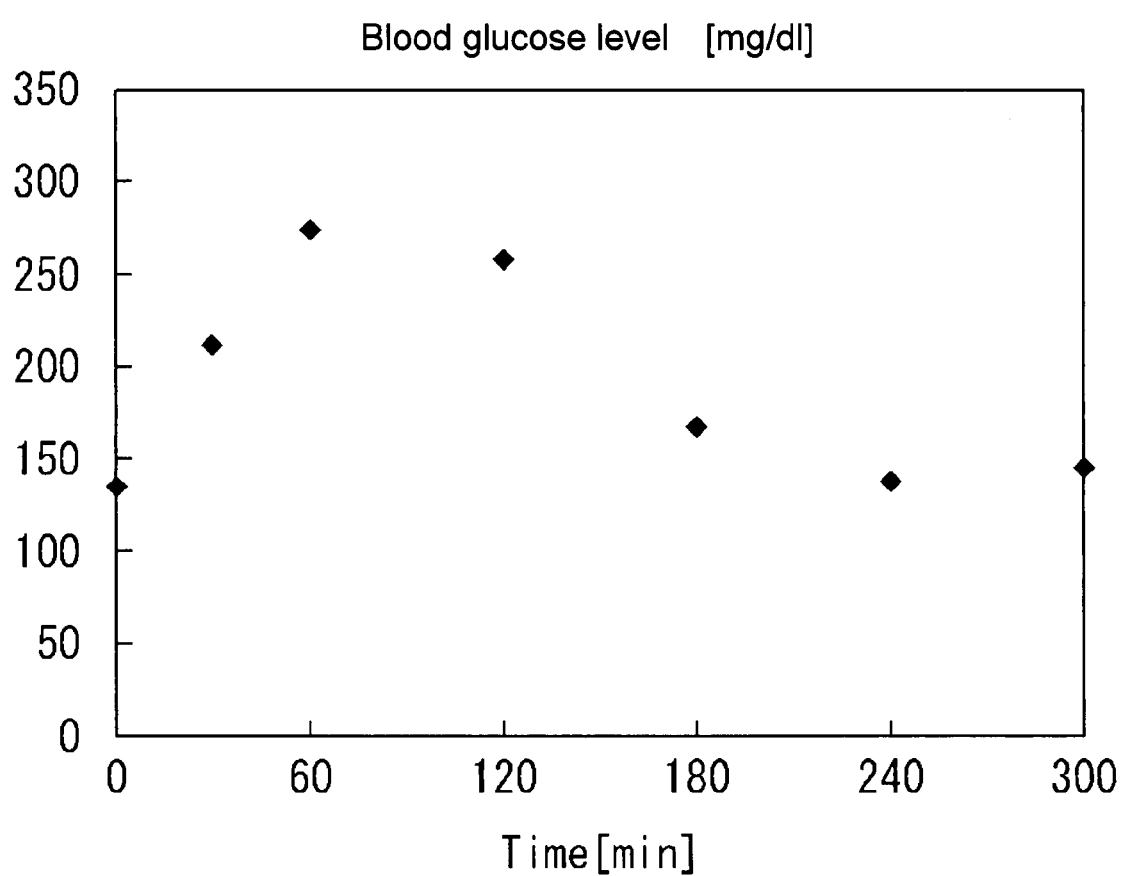
FIG. 12A is a graph showing actual measurement OGTT time-series data of blood glucose level for five hours.
Figure 12B:
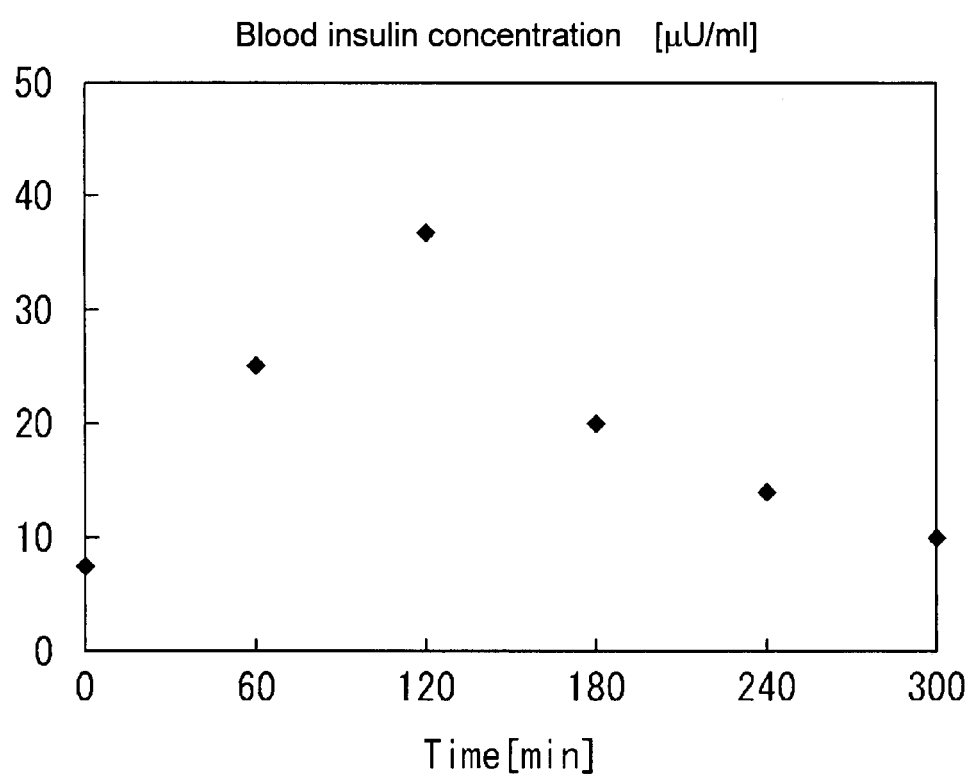
FIG. 12B is a graph showing actual measurement OGTT time-series data of insulin concentration for five hours.
Figure 13A:
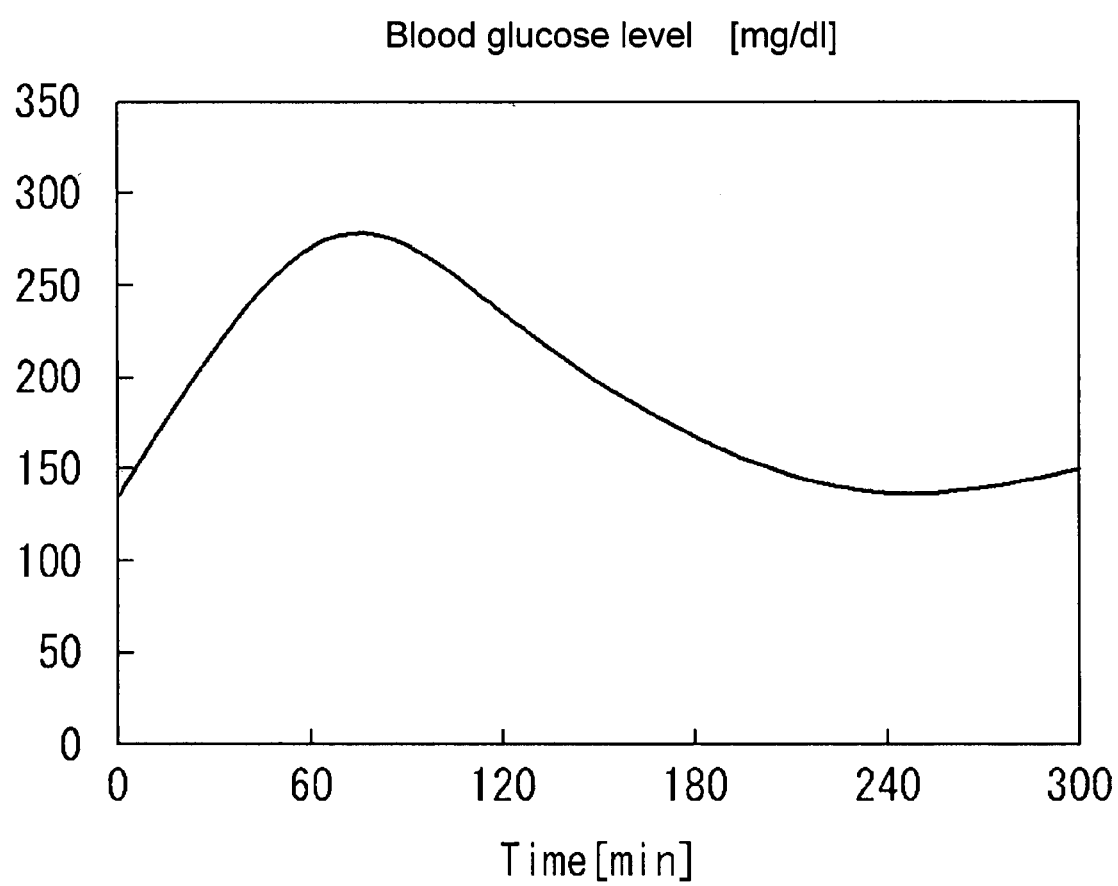
FIG. 13A is a graph showing the result related to the blood glucose level of the simulation using the data of FIGS. 12A and 12B.
Figure 13B:
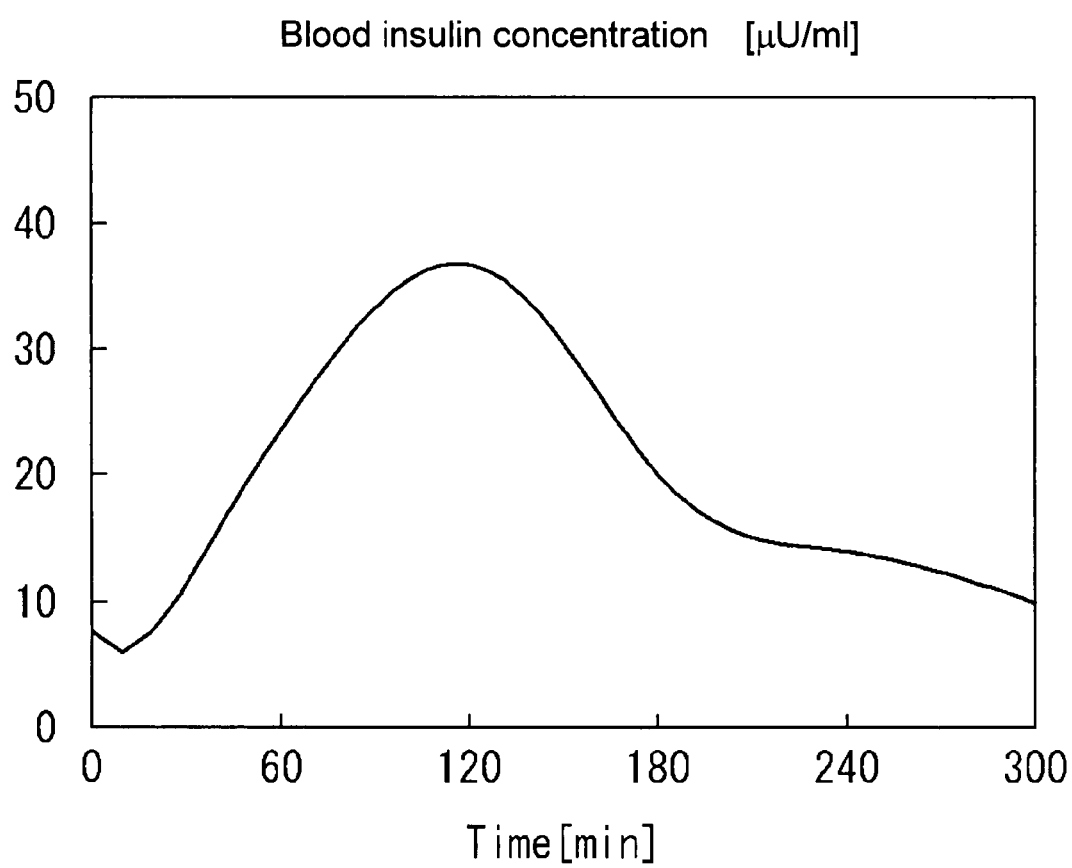
FIG. 13B is a graph showing the result related to the insulin concentration of the simulation using the data of FIGS. 12A and 12B.
Figure 14A:
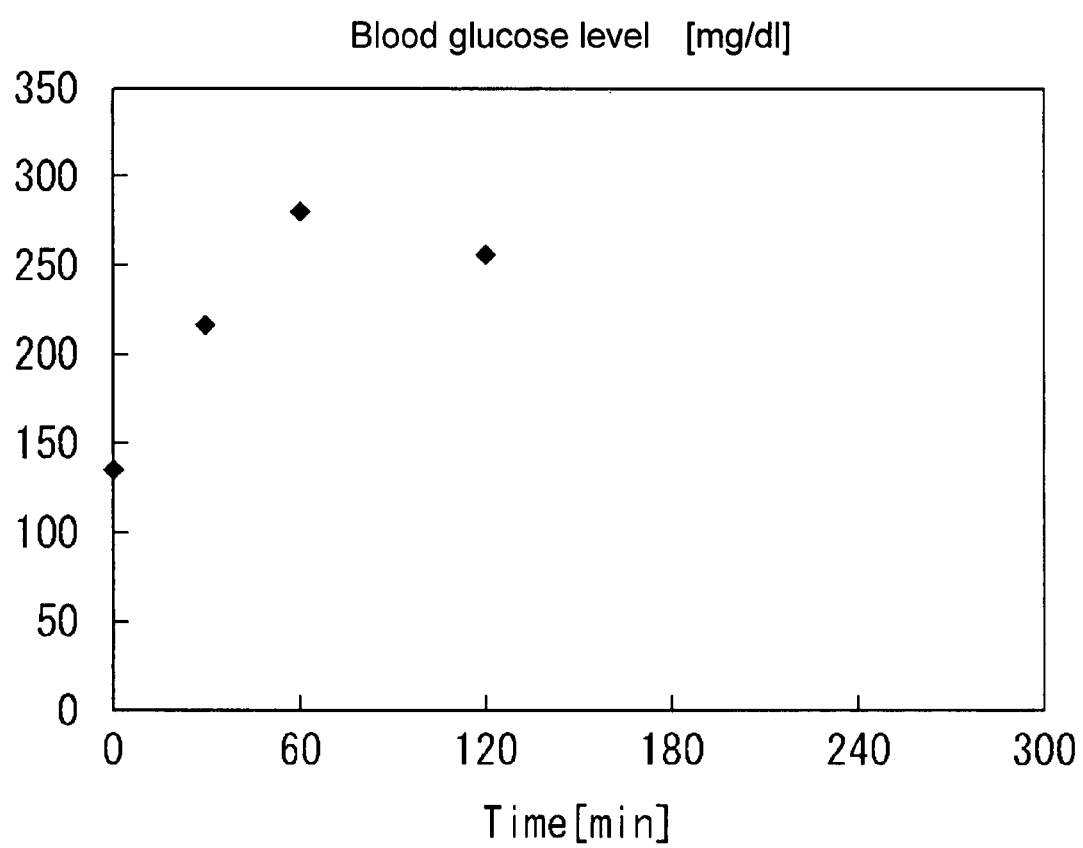
FIG. 14A is a graph showing actual measurement OGTT time-series data of blood glucose level for two hours.
Figure 14B:
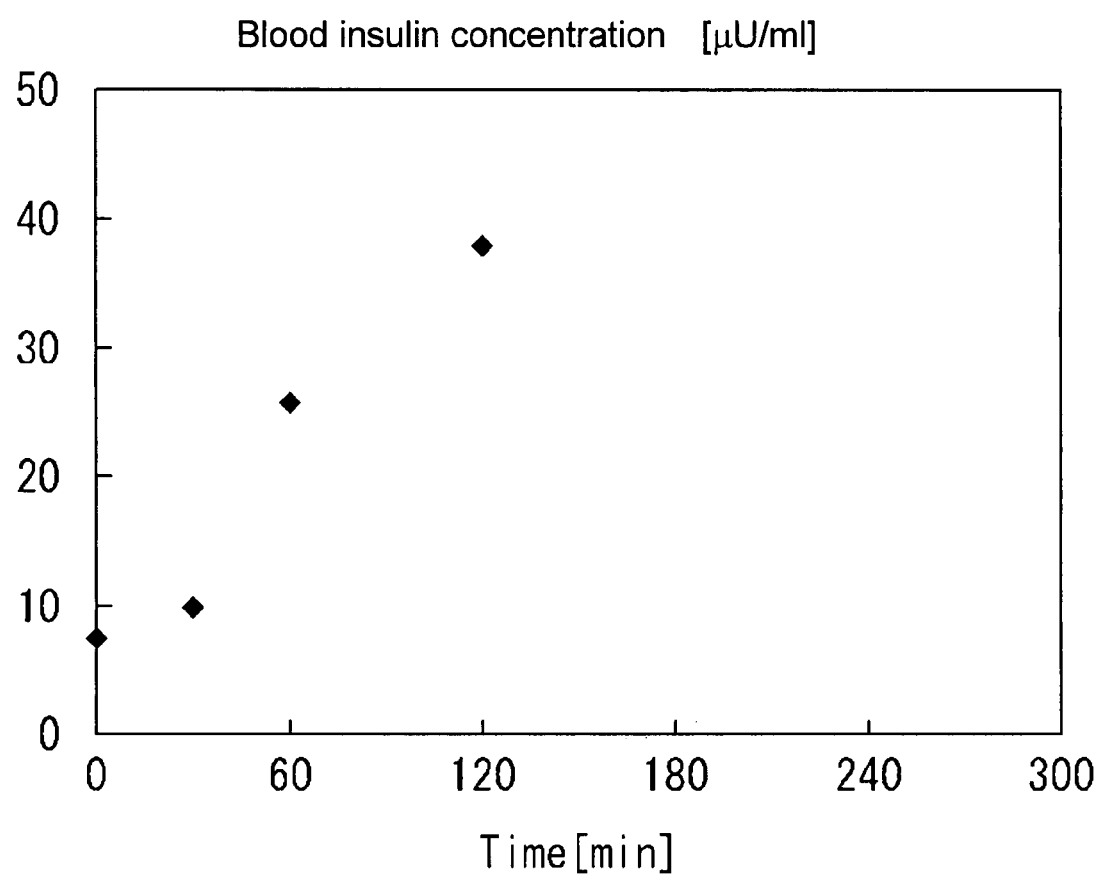
FIG. 14B is a graph showing actual measurement OGTT time-series data of insulin concentration for two hours.
Figure 15A:
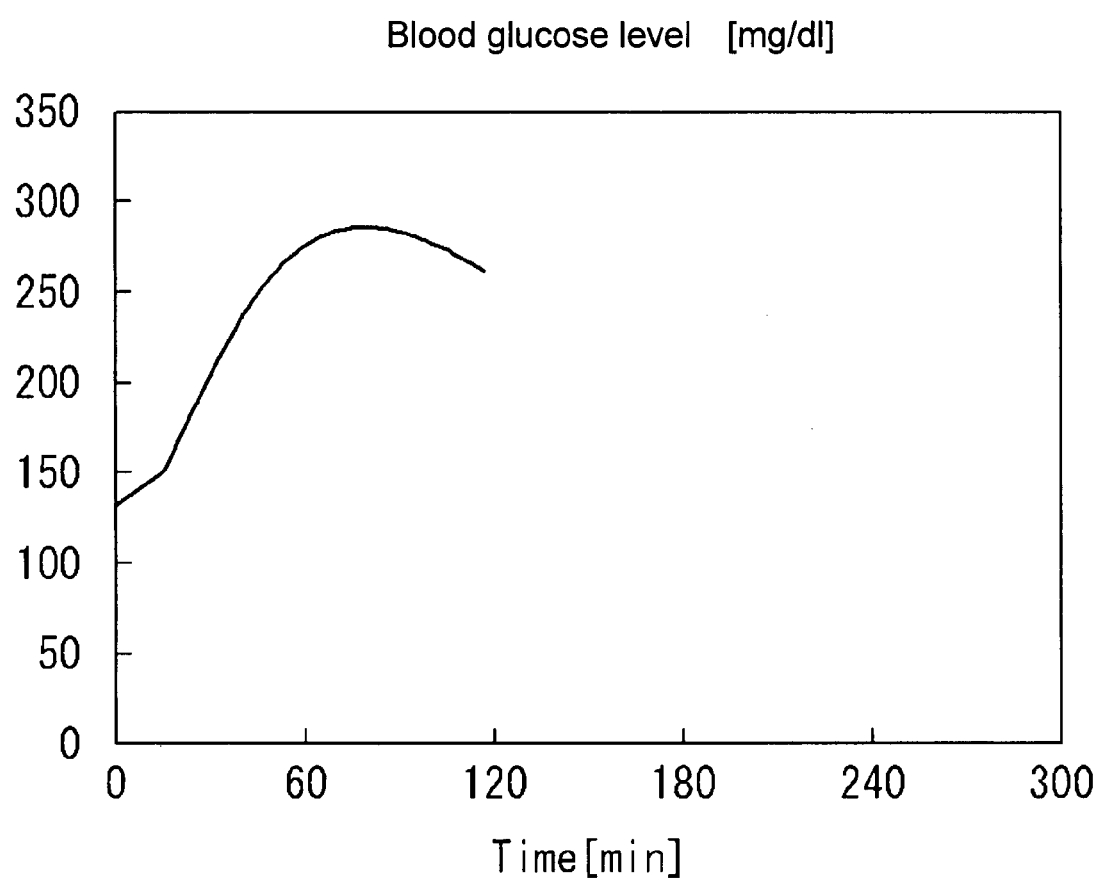
FIG. 15A is a graph showing the result related to the blood glucose level of the simulation using the data of FIGS. 14A and 14B.
Figure 15B:
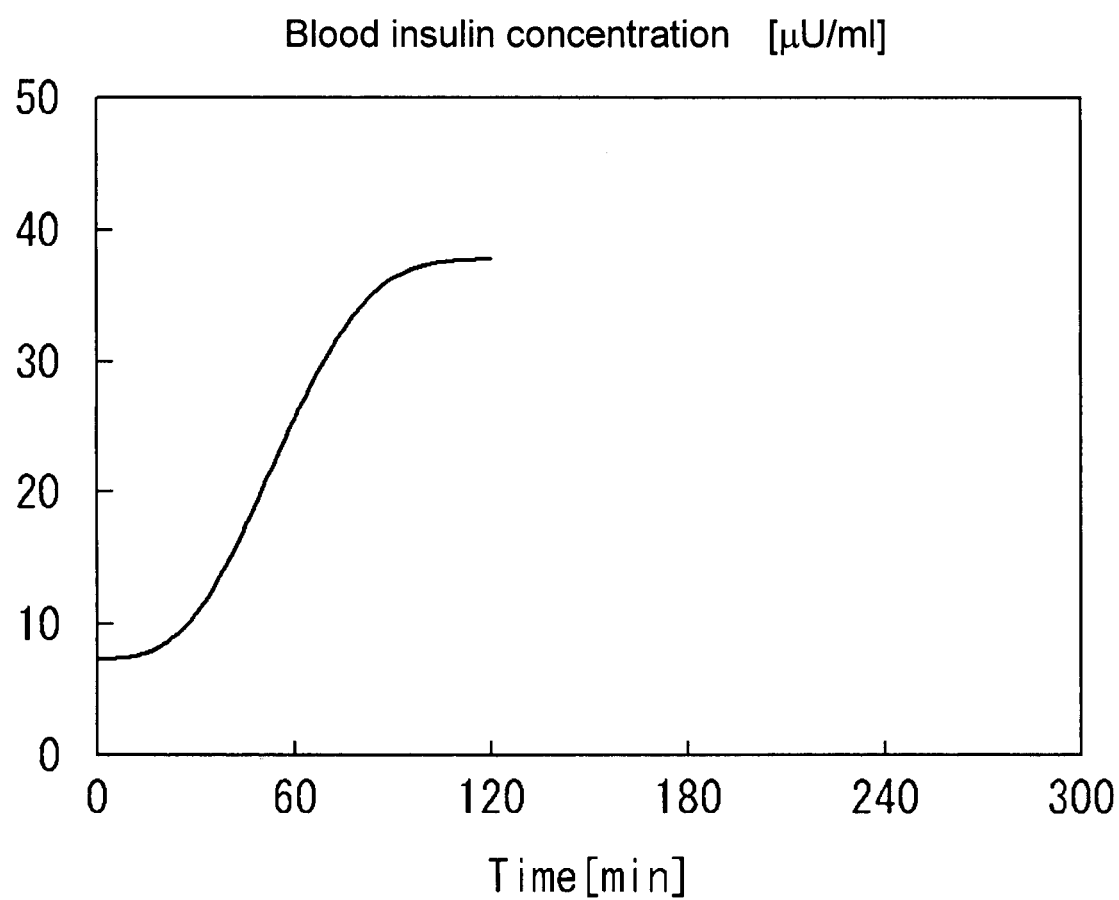
FIG. 15B is a graph showing the result related to the insulin concentration of the simulation using the data of FIGS. 14A and 14B.

FIGS. 12A and 12B are actual measurement OGTT time series data for 300 minutes, where FIG. 12A shows change in blood glucose level and FIG. 12B shows change in insulin concentration. FIGS. 13A and 13B show the results of simulation using the data of FIGS. 12A and 12B, where FIG. 13A shows change in blood glucose level and FIG. 13B shows change in insulin concentration. FIGS. 14A and 14B are actual measurement OGTT time series data for 120 minutes, where FIG. 14A shows change in blood glucose level and FIG. 14B shows change in insulin concentration. FIGS. 15A and 15B show the results of simulation using the data of FIGS. 14A and 14B, where FIG. 15A shows change in blood glucose level and FIG. 15B shows change in insulin concentration.

Figure 16A:
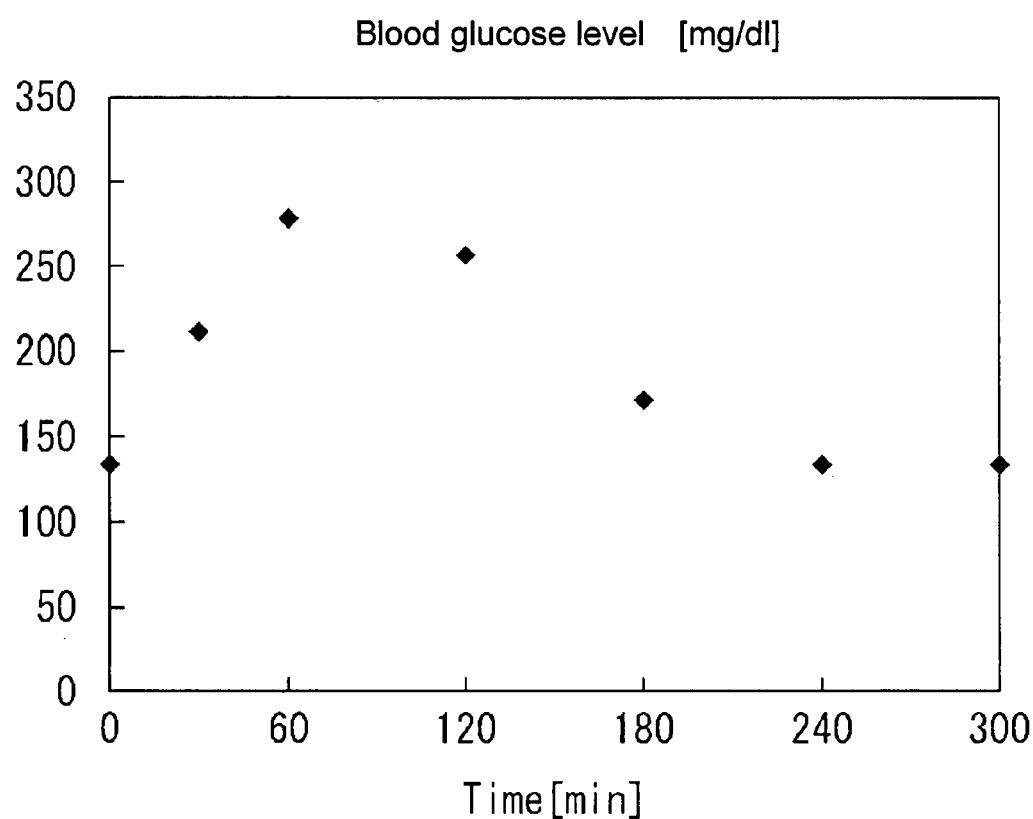
FIG. 16A is a graph showing reference data in which values of third hour, fourth hour, and fifth hour after the start of measurement are obtained through interpolation on the data of FIG. 14A.
Figure 16B:
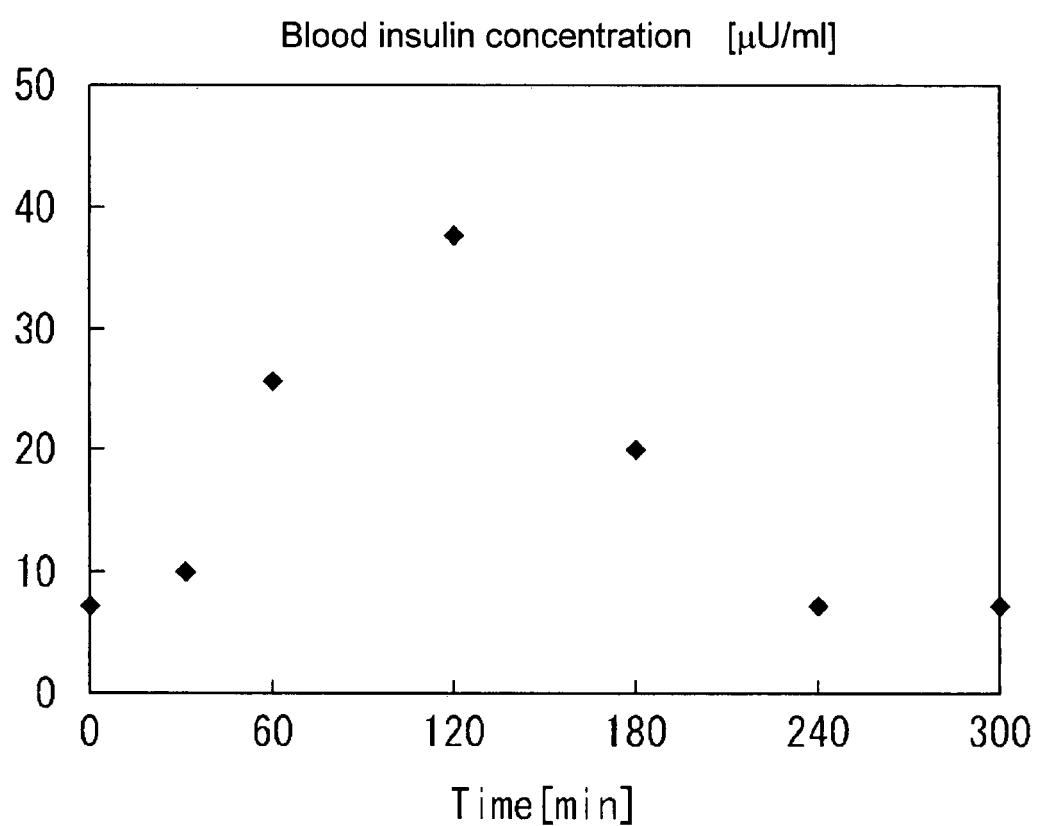
FIG. 16B is a graph showing reference data in which values of third hour, fourth hour, and fifth hour after the start of measurement are obtained through interpolation on the data of FIG. 14B.
Figure 17A:
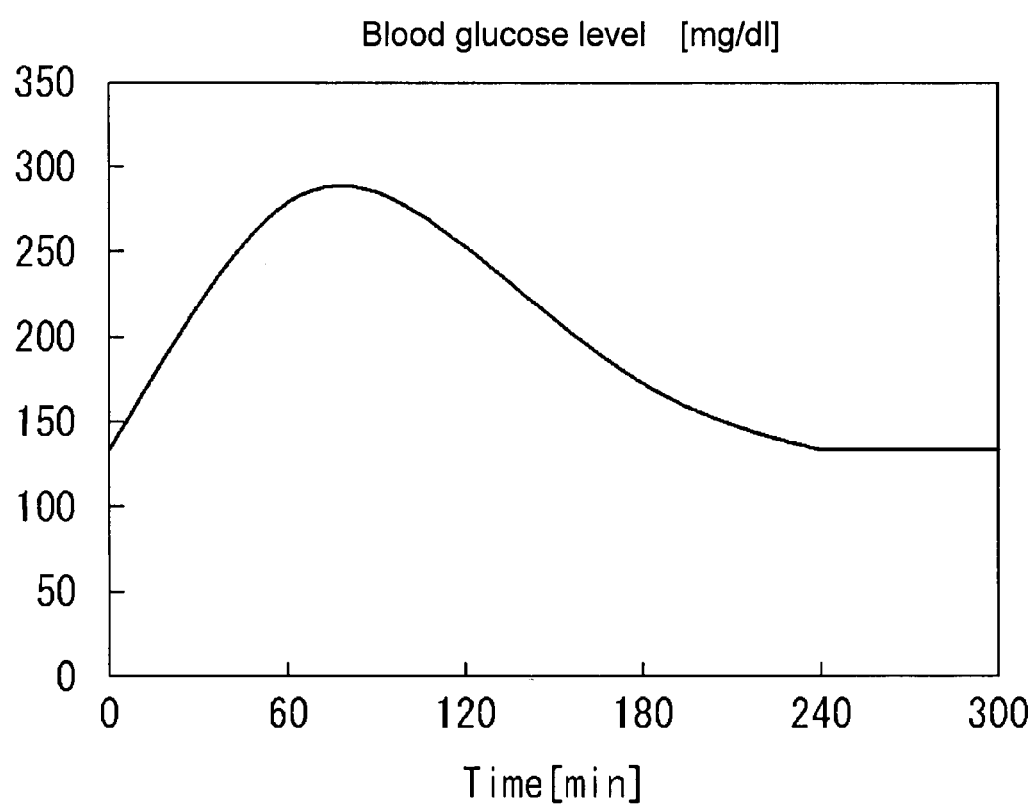
FIG. 17A is a graph showing the result related to the blood glucose level of the simulation using the data of FIGS. 16A and 16B.
Figure 17B:
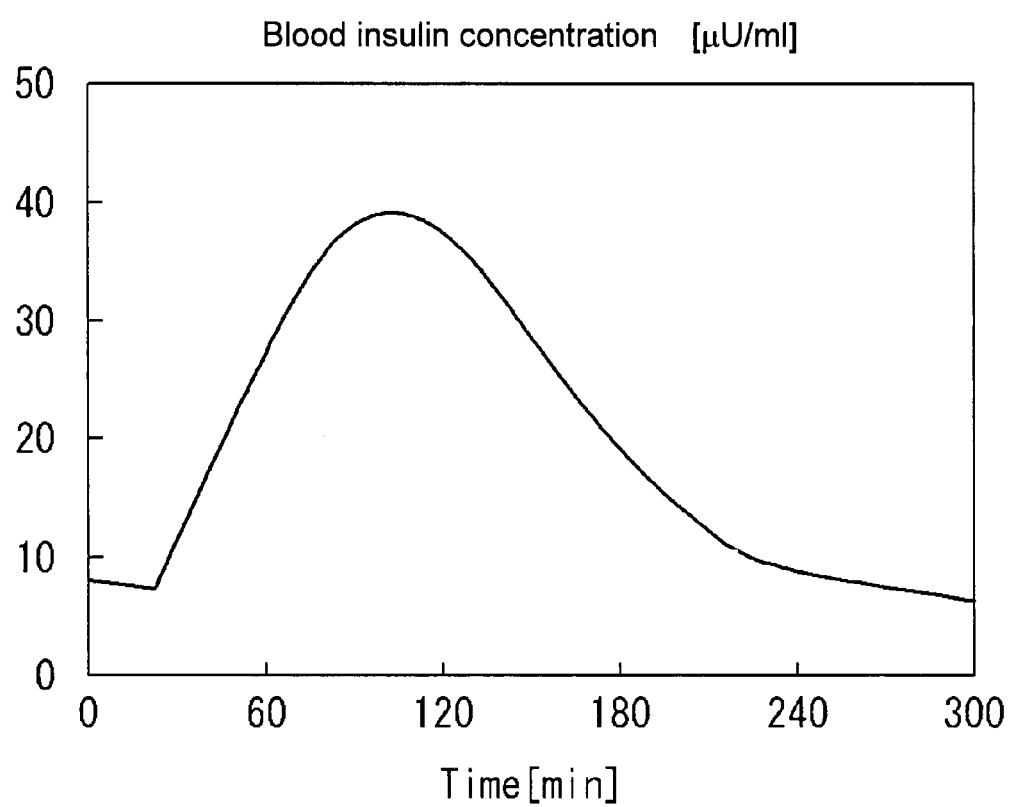
FIG. 17B is a graph showing the result related to the insulin concentration of the simulation using the data of FIGS. 16A and 16B.

In the case of FIGS. 14A, 14B, 15A, and 15B, the data collecting time is shorter than in the case of FIGS. 12A, 12B, 13A, and 13B, and the change in blood glucose level and insulin concentration in the biological body may only be partially observed, and thus the precision of the parameters of the biological model inevitably becomes lower than in the case of FIGS. 12A, 12B, 13A, and 13B. However, the precision may be enhanced by generating the values of third hour (180 min,), fourth hour (240 min.), and fifth hour (300 min.) after the start of measurement through interpolation, as shown in the examples in FIGS. 16A and 16B. In the example shown in FIGS. 16A and 16B, the blood glucose level and the insulin concentration both are assumed to return to the state substantially before glucose load after four hours have elapsed from after the glucose load due to homeostasis of the biological body, and thus the blood glucose level and the insulin concentration of the fourth hour and the fifth hour after the start of glucose load are both assumed to be equal to the value before the glucose load (time of start of data acquisition). Regarding the third hour after the start of the glucose load, the reference data generating section of the present system 100 obtains the blood glucose level and the insulin concentration through spline interpolation method. FIGS. 17A and 17B show the result of simulation using the reference data including the interpolated data obtained as above and the actual measurement data, where FIG. 17A shows change in blood glucose level and FIG. 17B shows change in insulin concentration.

The following table shows some of the parameters in the parameter set of the biological model obtained as the reference data using the actual data for five hours, the actual data for two hours, and the actual data for two hours added with extrapolation/interpolation data. The two columns on the right side of table 2 are indexes representing to what extent the parameters obtained using the actual data for two hours and the actual data for two hours added with extrapolation/interpolation data differ with respect to the reference parameter (parameter obtained using actual data for five hours) with the parameter (highest precision of three types of parameters) obtained using the actual data for five hours as the reference. The parameter is closer to the reference parameter, that is, higher precision is obtained the smaller the index value. Although the index is slightly large for parameter "H" from table 2, the other parameters "X0" and "Kb" are significantly smaller, and thus the precision of the parameter enhances as a whole when the extrapolation/interpolation data are added compared to the actual data for two hours.

[Template Matching: Step S3]

Next, the present system 100 matches the reference data generated by the reference data generating section with the template of template database DB. As shown in FIG. 9, the template database DB is preliminarily stored with a plurality sets of data, which are biological model output values T1, T2, . . . as a template and parameter set PS#01, PS#02 . . . correspondent to the output value to generate the output value. To make up a pair of output value and parameter set, a random output value is assigned by an appropriate parameter set, or on the contrary, a biological model output at the time when a random parameter set is selected is obtained by the biological simulation.

Figure 10A:
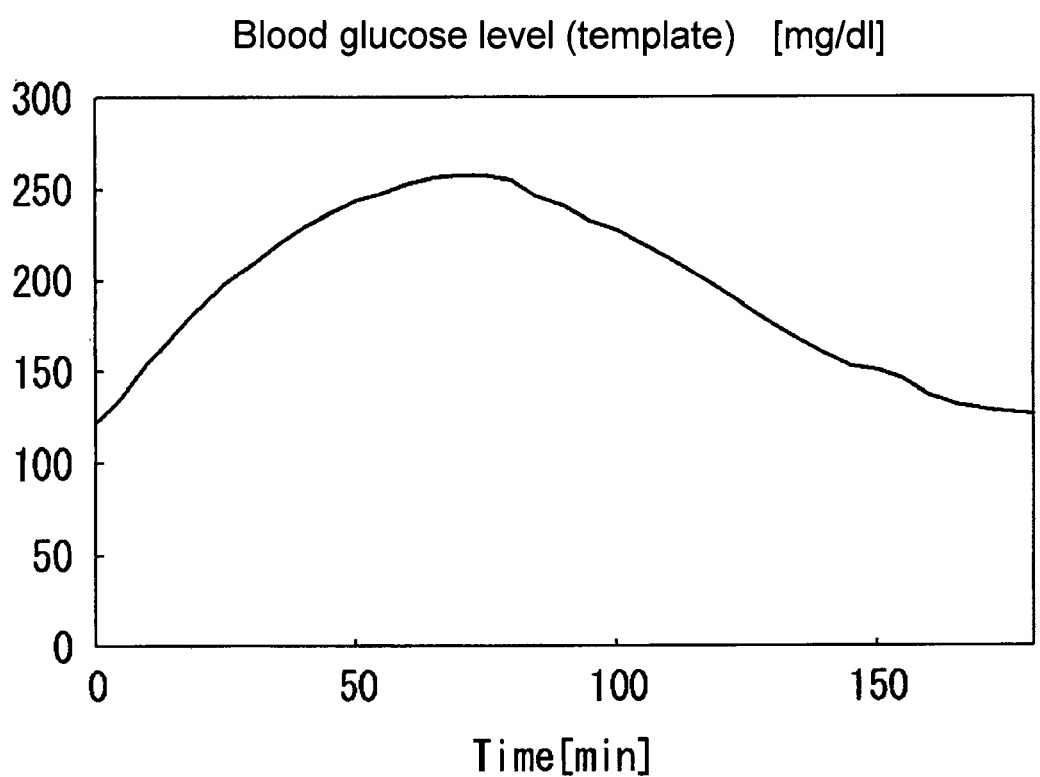
FIG. 10A is template data of blood glucose level.
Figure 10B:
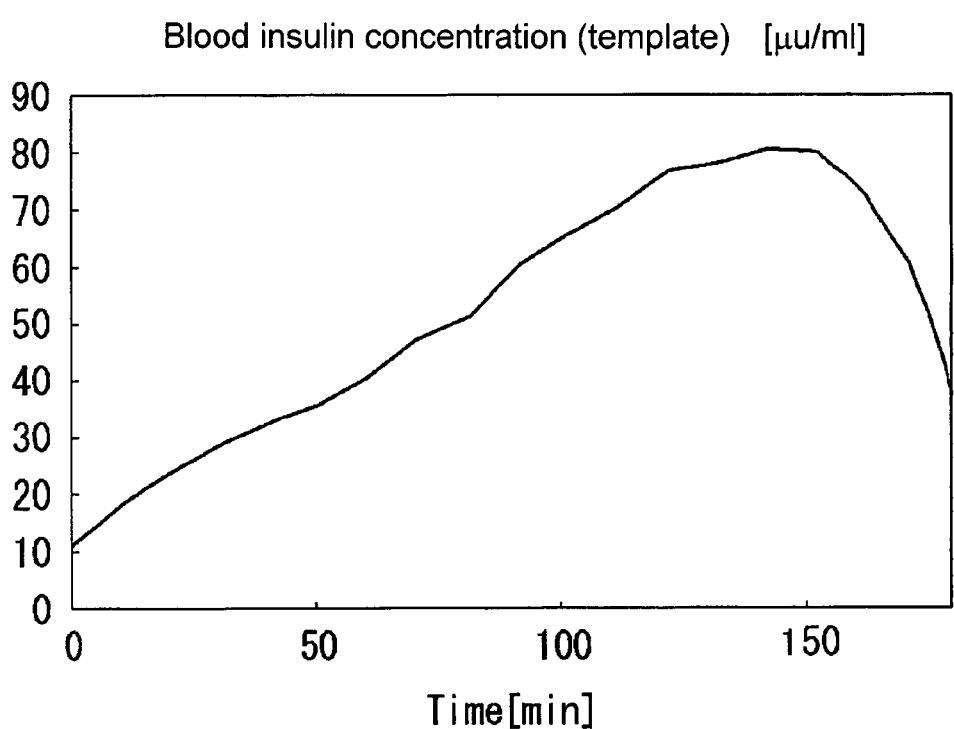
FIG. 10B is template data of insulin concentration.

FIG. 10A and FIG. 10B shows examples of the template T1. FIG. 10A shows data of change in blood glucose level for three hours as a template, which is time-series data corresponding to time course of the blood glucose level BG(t), one of output items in the biological model shown in FIGS. 2 to 6. FIG. 10B shows data of change in blood insulin concentration for three hours as a template, which is time-series data corresponding to time course of blood insulin concentration $I1(t)$, one of output items in the biological model shown in FIGS. 2 to 6. When the data for five hours, for example, are generated as the reference data, such reference data are compared with the template including the data for five hours stored in the template database DB.

The system 100 computes similarity between each time-series datum of the above-mentioned template database DB and the reference data obtained in the above manner. The similarity is obtained by obtaining error summation. The error summation is obtained by the following formula.

$$\text{Error summation} = \alpha\Sigma|BG(0) - BGt(0)| + \beta\Sigma|PI(0) - PIt(0)| +$$
$$\alpha\Sigma|BG(1) - BGt(1)| + \beta\Sigma|PI(1) - PIt(1)| +$$
$$\alpha\Sigma|BG(2) - BGt(2)| + \beta\Sigma|PI(2) - PIt(2)| +$$
$$\ldots$$
$$= \alpha\{\Sigma|BG(t) - BGt(t)|\} + \beta\{\Sigma|PI(t) - PIt(t)|\}$$

where
BG: input data blood glucose level [mg/dl]
PI: input data blood insulin concentration [μU/ml]
BGt: template blood glucose level[mg/dl]
PIt: template blood insulin concentration [μU/ml]
t: time[minute]
Here, α and β are coefficient used for normalization $\alpha = 1/\text{Average}\{\Sigma BG(t)\}$ $\beta = 1/\text{Average}\{\Sigma PI(t)\}$ The average of the formula shows average level to all templates stored in the template database DB.

| Parameter | Data for 300 minutes | Data for 120 minutes | Extrapolation/ interpolation data | $|120_{min} - 300_{min}| \div 300_{min}$ | $|\text{Extra/Interpolation} - 300_{min}| \div 300_{min}$ |
|---|---|---|---|---|---|
| BETA | 0.129 | 0.12 | 0.138 | 0.069 | 0.069 |
| H | 111 | 98 | 126 | 0.11 | 0.13 |
| ALPHA | 0.087 | 0.058 | 0.073 | 0.33 | 0.16 |
| X0 | 18 | 10 | 22 | 0.44 | 0.22 |
| Kb | 0.0038 | 0.0069 | 0.0049 | 0.81 | 0.28 |
| A2 | 0.051 | 0.035 | 0.05 | 0.31 | 0.019 |

Figure 11A:
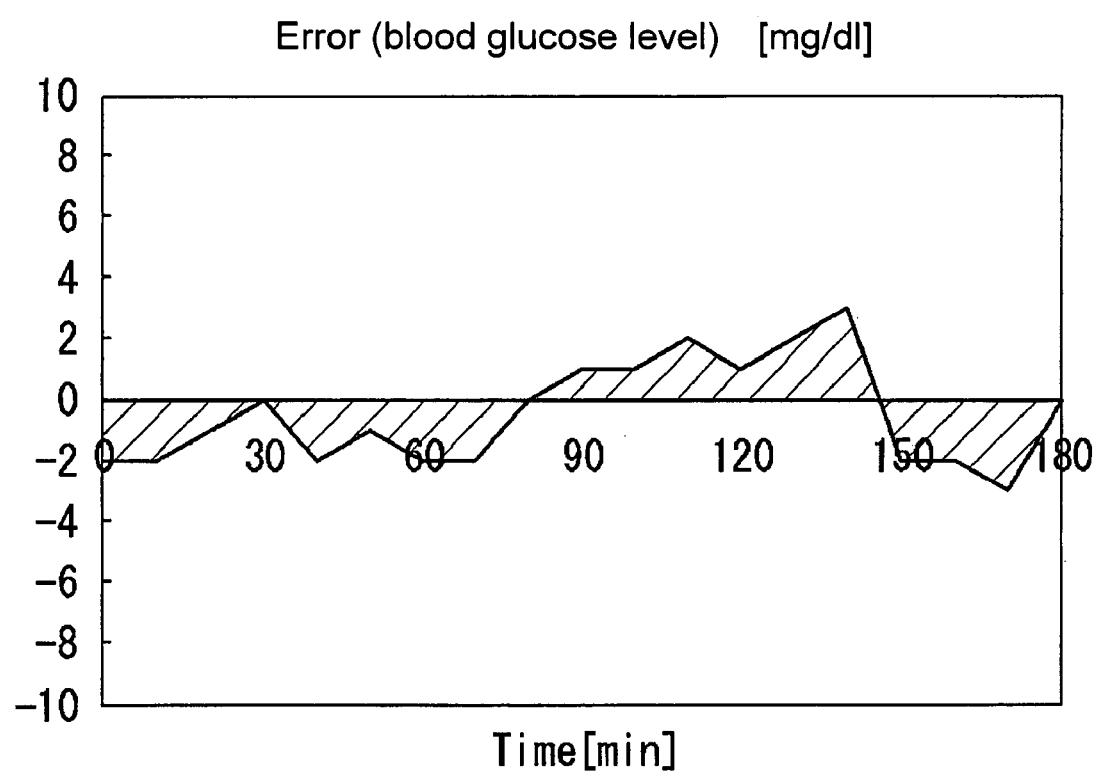
FIG. 11A is a diagram showing an error sum of OGTT time-series data against a template of blood glucose level.
Figure 11B:
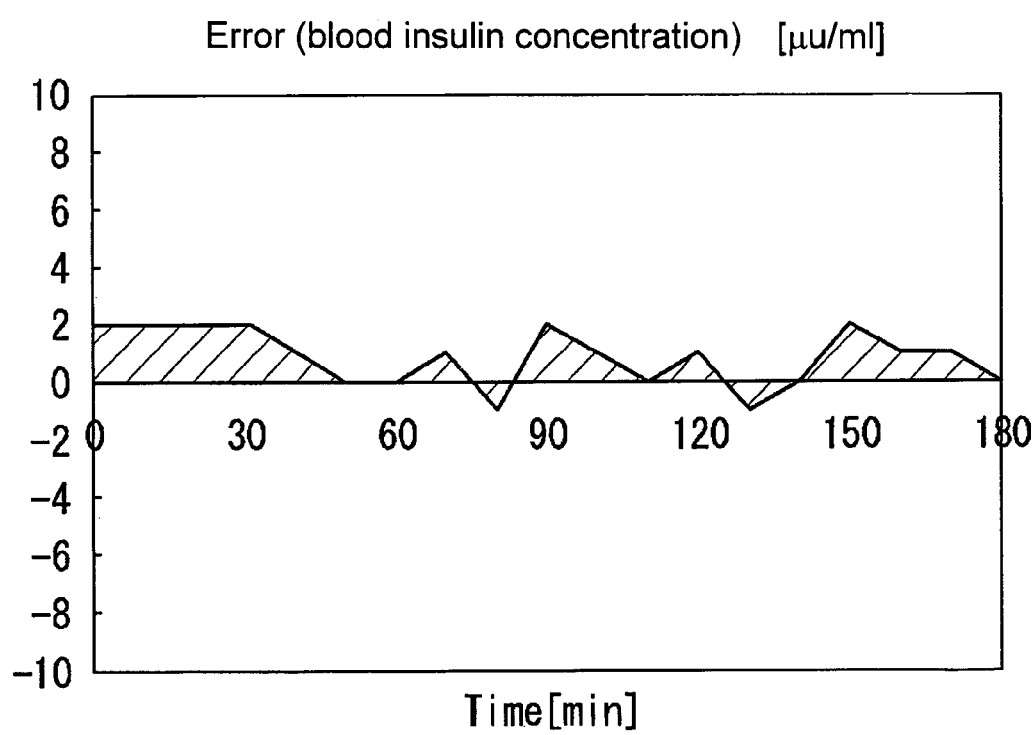
FIG. 11B is a diagram showing an error sum of OGTT time-series data against a template of insulin concentration.

FIG. 11A and FIG. 11B show error summation (no normalization) of the reference data with respect to the template T1. More specifically, FIG. 11A shows an error between the blood glucose level of FIG. 8A and the blood glucose level of FIG. 10A. FIG. 11B shows an error between the blood insulin concentration of FIG. 8B and the blood insulin concentration of FIG. 10B.

Based on FIG. 8A and FIG. 8B input data (date in the range of 0 to 180 minutes every 10 minutes) and FIG. 10A and FIG. 10B template T1, $$\Sigma_1{}^1|BG(t)-BGt(t)|_1{}^1=29$$

$$\Sigma_1{}^1|PI(t)-PIt(t)|_1{}^1=20$$

where, provided $\alpha=0.00035$, $\beta=0.00105$
  error summation=(0.00035×29)+(0.00105×20)
  =0.03115

Thus, CPU 100a obtains an error summation to each template in the template database DB, and determines the template having the minimum error summation (similarity). Thus, CPU 100a determines the template which is the most approximate to the reference data (Step S3).

[Acquisition of Parameter Set: Step 4]

Further, in a step S4, the system 100 obtains from template database DB a parameter set corresponding to the template which has been determined in the step S3. That means, a parameter set PS#01 corresponding to the template T1 is obtained (Refer to FIG. 9). The table below exemplifies the specific numeral values of the parameter values included in the parameter set PS#01 obtained by the above-mentioned way.

Parameter set PS#01 corresponding to template T1

| | Parameter | Value | Unit |
|---|---|---|---|
| Pancreas | h | 92.43 | [mg/dl] |
| | α | 0.228 | [1/min] |
| | β | 0.357 | [(μU/ml) · (dl/mg) · (1/min)] |
| | M | 1 | [1/min] |
| | X(0) | 336.4 | [μU/ml] |
| | Y(0) | 4.4 | [(μU/ml) · (1/min)] |
| Insulin kinetics | A1 | 0.025 | [1/min] |
| | A2 | 0.042 | [1/min] |
| | A3 | 0.435 | [1/min] |
| | A4 | 0.02 | [1/min] |
| | A5 | 0.394 | [1/min] |
| | A6 | 0.142 | [1/min] |
| Peripheral tissues | Kb | 0.009 | [1/min] |
| | Kp | 5.28E−05 | [(ml/μU) · (1/min)] |
| | u | 0.6 | |
| Liver | A7 | 0.47 | |
| | Kh | 0.0000462 | [(ml/μU) · (1/min) · (dl/kg)] |
| | b2 | 1.1 | |
| | r | 0.98 | |
| | α2 | 0.228 | |
| | I4off | 5 | [μU/ml] |

The method of generating the parameter set (biological model) is not limited to template matching as described above. For instance, the parameter set may be generated through genetic algorithm. That is, genetic algorithm may be applied in generating the parameter set, where an initial group of parameter set is produced at random, and selection/chiasm/mutation process is performed on the parameter set (individual) contained in the initial group to generate a new child group. In the method of generating the parameter set through genetic algorithm, the parameter set that outputs the simulated response close to the input biological response (test result) is used among the generated parameter sets. Thus, the specific generating method of the biological model generating section is not particularly limited as long as the biological model that outputs simulated response simulating the input biological response can be generated.

Regarding the blood glucose level and the insulin concentration on the fourth hour and the fifth hour, the parameter set may be obtained in the following manner in addition to setting to the value before glucose load as described above.

First, the state after a constant time has elapsed (e.g., after four hours have elapsed from start of measurement) is randomly set to a value of an arbitrary range of the values before the glucose load (start of measurement). For instance, the state is set to a value within twenty percent of the values of before the glucose load. Specifically, when the blood glucose level before the glucose load is 100[mg/dl] and the insulin concentration before the glucose load is 8[μU/ml], the values are set to blood glucose level of 110[mg/dl] and the insulin concentration of 7.5[μU/ml].

Subsequently, interpolation is performed for the remaining values for the third hour and the fifth hour to obtain the reference data, and the parameter sets are obtained according to the steps S3 to S4 using the reference data. The setting of the values of the arbitrary range is appropriately changed, and the above processes are repeated to obtain a great number of parameter sets.

The great amount of obtained parameter sets are then clustered based on similarity to narrow the parameter sets to an arbitrary number of clusters. Specifically, an arbitrary number of clusters are generated through hierarchical cluster analysis. The great number of parameter sets does not have completely random values in which the parameter values are substantially evenly dispersed, but generally have a local distribution in which the approximate parameter values are collected with each other, and thus the process of generating the "cluster" in which the parameter set groups having approximate parameter values are grouped is performed.

The present system performs (1) standardization process of the parameter set and (2) hierarchical cluster analysis process for cluster generating process. The standardization (normalization) process of the parameter set is a pre-process for the hierarchical cluster analysis process. The standardization process is performed to eliminate the influence caused by difference in units/numerical value ranges between the parameters since each parameter has different unit/numerical value range. Calculation of the standardization is performed by the CPU 110a in the following manner as an example. The following equation (1) is used when standardizing the parameter P01 (parameter set is assumed to contain 19 parameters P01 to P19) of FIG. 18. The number of parameter sets obtained in the previously described process is 100.

$$nP01(\#i) = \frac{PS01(\#i) - \text{mean}(PS01)}{SD(PS01)} \quad (1)$$

where,
P01 (#i): parameter P01 of ith parameter set
nP01 (#1): standardized P01 (#i)
mean (PS01): average value of P01(#1) to P01(#100)
SD (PS01): standard deviation of P01(#1) to P01(#100)

An example of the result of the standardizing process using the equation similar to equation (1) for parameters P02 to P019 other than P01 is shown in FIG. 19.

Figure 20:
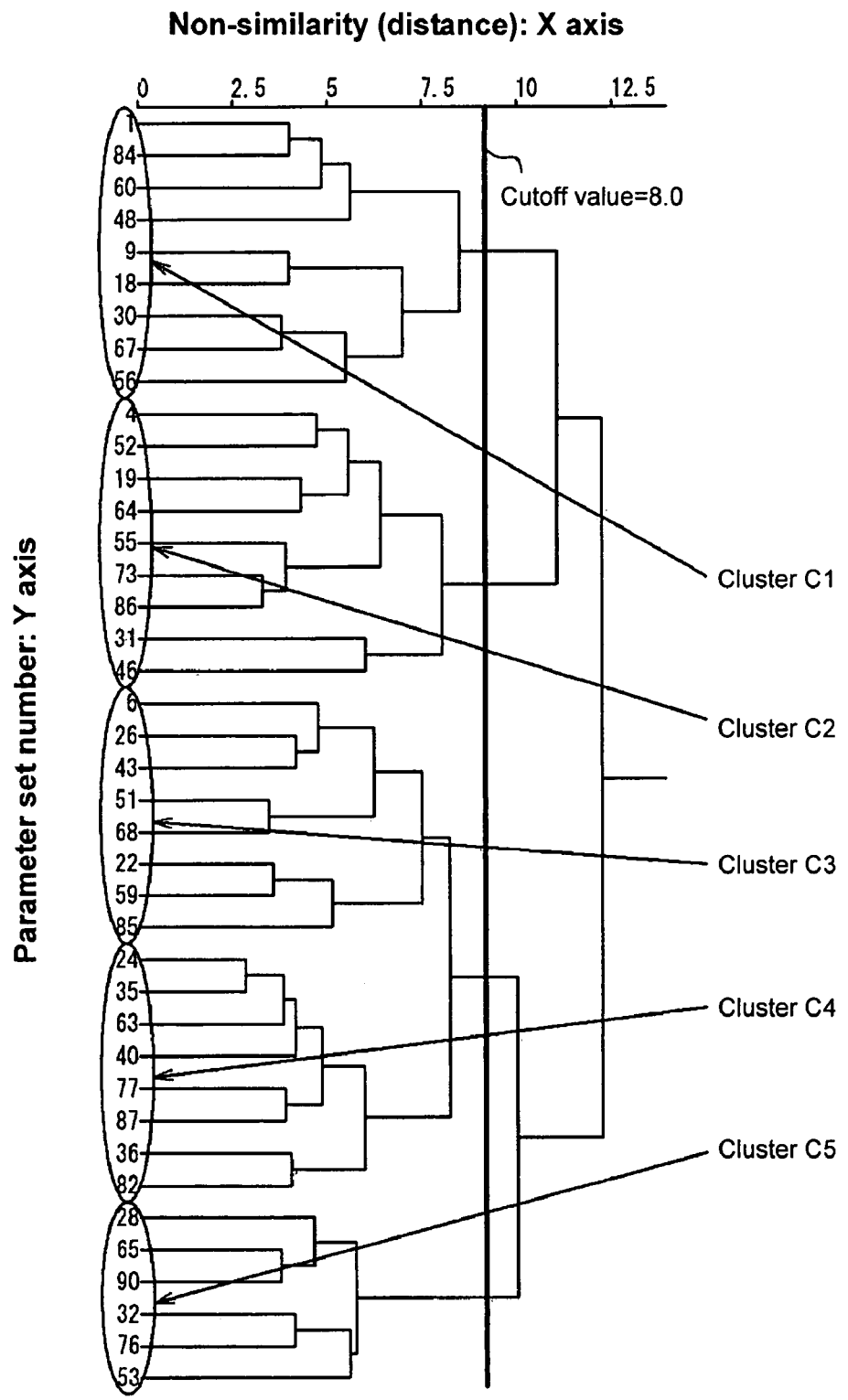
FIG. 20 is a dendrogram showing a cluster analysis result of the parameter sets.

Subsequently, the CPU 110a performs the process for the hierarchical cluster analysis with respect to the parameter set subjected to the standardizing process. FIG. 20 shows a dendrogram of the cluster analysis result. "Euclidean distance" is used as the reference on whether or not the individuals are similar, and the Ward method is used as a method of calculating the distance. If p (p: 1 to 19) parameters exist for n (n:1 to 100) individuals (parameter sets), each parameter is expressed as $X_{i1}, X_{i2}, \ldots, X_{ip}$ (i:1,2, ... ,n). Furthermore, n individuals each configure the cluster in the initial state, and n clusters are assumed to exist. The Euclidean square distance $d_{ij}^2$ between the clusters (individuals in the initial state) is calculated by equation (2).

$$d_{ij}^2 = \sum_{k=1}^{p} (X_{ik} - X_{jk})^2 \; (i, j, = 1, 2, \cdots, n) \qquad (2)$$

After the Euclidean square distance is obtained, the clusters having the closest distance are merged to form a new cluster. That is, when cluster a and cluster b merge to form a new cluster c, the distance between the clusters a, b before cluster a and cluster b are merged is assumed as dab, the distance between cluster a and another cluster x (x≠a, x≠b) as $dX_a$, and the distance between cluster b and another cluster x (x≠a, x≠b) as $d_{xb}$, the distance $d_{xc}$ between cluster c and another cluster x (x≠a, x≠b) after the merge is expressed as equation (3).

$$d_{xc}^2 = \{(n_X + n_a)/(n_X + n_C)\}d_{xa}^2 + \{(n_X + n_b)/(n_X + n_C)\}d_{xb}^2 + \qquad (3)$$
$$\{-n_X/(n_X + n_C)\}d_{ab}^2$$

where, $n_a$ is the number of individuals (number of parameter set candidates) contained in cluster a. This is the same for $n_b$, $n_c$, and $n_x$.

The total number of clusters reduces by one when two clusters merge. The merging process is repeated until the total number of clusters becomes one, and the cluster analysis is terminated. The calculated distance d indicates the non-similarity between the individuals (parameter set candidates), where the individuals are more similar the smaller the distance. FIG. 20 shows one part of the dendrogram of when the non-similarity (distance) between the parameter set candidates is shown on the X axis and the parameter set numbers are shown on the Y axis.

In FIG. 20, for example, the non-similarity between the parameter set PS#01 and the parameter set P#84 is about 4×. When collecting the parameter set candidates within non-similarity of 8 to generate a cluster, the cutoff value is assumed to be 8, as shown in FIG. 20, and the parameter set groups at the end (left side of cutoff in FIG. 20) of each branch cut at the cutoff value respectively form the cluster. FIG. 20 shows five clusters C1 to C5 out of a total of ten formed clusters.

The parameter set candidates belonging to the generated cluster have approximate values, and thus have similar function when applied to the biological model. The CPU 110*a* then performs the process of generating a single parameter set that represents the cluster. In order to generate the single parameter set that represents the cluster (cluster representing parameter set), the average value of each parameter of the parameter set belonging the cluster is set as each parameter value of the cluster representing parameter set. In obtaining the average value of each parameter, weighing based on similarity (non-similarity) may be performed instead of a simple averaging. The parameter set candidate is obtained for every cluster by the above processes, and a hundred sets of parameter sets are narrowed to ten parameter set candidates which parameter values are not approximate to each other.

The interpolation method of the data is not particularly limited in the present invention, and other known interpolation methods such as linear interpolation may be appropriately adopted other than the spline interpolation method described above. Interpolation is performed only for the values on the third hour in the above description for simplification, but the reference data may be obtained at an arbitrary time interval (e.g., ten-minute interval) between the actual measurement data through interpolation.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A simulation system for simulating a function of a biological organ associated with diabetes, the simulation system comprising:
   a computer readable storage medium having stored therein instructions executable by a processor for performing the steps of:
   storing a mathematical model that comprises a plurality of parameters and represents a function of a biological organ associated with diabetes;
   receiving input of time-series actual measurement data representing blood glucose and/or blood insulin levels obtained by measuring the biological response of a subject;
   estimating data representing blood glucose and/or blood insulin levels of the subject at a time point that is different from the time-series actual measurement data,
   generating time-series reference data representing the biological response of the subject based on the time-series actual measurement data and the estimated data;
   acquiring a plurality of sets of parameter values of the mathematical model;
   comparing each virtual biological response generated when each of the plurality of sets of parameter values is applied to the mathematical model with the generated time-series reference data; and
   selecting one of the plurality of sets of parameter values based on the comparison so as to generate a plurality of parameter values wherein the mathematical model for the subject represents the function of the biological organ when the plurality of parameter values are applied to the model.

2. The simulation system according to claim 1, wherein the time-series actual measurement data is obtained by measuring the biological response of the subject at time intervals, and
   the time point for estimating data is between the time interval of the time-series actual measurement data.

3. The simulation system according to claim 1, wherein the time-series actual measurement data is obtained by measuring the biological response of the subject in a first time period,
   the time point for estimating data is outside the first time period, and the time-series reference data is generated with respect to a second time period longer than the first time period.

4. The simulation system according to claim 3, wherein the estimating data comprises estimating data at the end of the second time period as being substantially equal with the actual measurement data at the start of the first time period, and the time-series reference data is generated by interpolation based on the time-series actual measurement data and the estimated data at the end of the second time period.

5. The simulation system according to claim 4, wherein the generating time-series reference data comprises obtaining a curve that substantially matches the time-series actual measurement data and the estimated data at the end of the second time period.

6. The simulation system according to claim 1, wherein the mathematical model comprises a block representing the function of the biological organ associated with metabolism of glucose and/or insulin.

7. The simulation system according to claim 1, wherein the comparing comprises obtaining error summations between the generated time-series reference data and each virtual biological response generated when each of the plurality of sets of parameter values is applied to the mathematical mode, and the selected set of parameter values correspond to a virtual biological response having a minimum error summation from among the obtained error summations.

8. The simulation system according to claim 1, further comprising instructions for performing the steps of:
    storing the plurality of sets of parameter values and a plurality of template data representing the virtual biological responses, wherein each of the virtual biological responses represented by each of the template data corresponds to each of the sets of parameter values,
    wherein, the acquiring comprises reading out the stored set of parameter values and the template data.

9. The simulation system according to claim 1, wherein the acquiring comprises,
    generating a plurality of initial groups of the parameter values; and
    executing a genetic algorithm on the plurality of initial groups of the parameter values, and generating a plurality of sets of parameter values.

* * * * *